US011263850B2

(12) United States Patent
Jafri

(10) Patent No.: US 11,263,850 B2
(45) Date of Patent: Mar. 1, 2022

(54) SYSTEMS AND METHODS FOR MANAGING INFECTIOUS DISEASE DISSEMINATION

(71) Applicant: AAJ Computer Services, Inc., Fort Lauderdale, FL (US)

(72) Inventor: Amjad Shamim Jafri, Parkland, FL (US)

(73) Assignee: AAJ Computer Services, Inc., Fort Lauderdale, FL (US)

( * ) Notice: Subject to any disclaimer, the term of this patent is extended or adjusted under 35 U.S.C. 154(b) by 0 days.

(21) Appl. No.: 17/320,481

(22) Filed: May 14, 2021

(65) Prior Publication Data

US 2021/0350649 A1 Nov. 11, 2021

Related U.S. Application Data

(63) Continuation-in-part of application No. 17/112,386, filed on Dec. 4, 2020, now Pat. No. 11,011,003.
(Continued)

(51) Int. Cl.
*G07C 9/20* (2020.01)
*G07C 9/27* (2020.01)
(Continued)

(52) U.S. Cl.
CPC .............. *G07C 9/27* (2020.01); *G06K 7/1417* (2013.01); *G06K 19/06037* (2013.01);
(Continued)

(58) Field of Classification Search
CPC ........ G07C 9/215; G07C 9/29; G06K 7/1417; G06Q 50/265; H04W 4/029; G16H 40/20;
(Continued)

(56) References Cited

U.S. PATENT DOCUMENTS 11,151,820 B1 * 10/2021 Klein .................... G16H 10/40
2020/0134154 A1    4/2020 Cornick et al.
2020/0372743 A1 * 11/2020 Miller ............... G06K 9/00288

OTHER PUBLICATIONS

Abbott's Fast, $5, 15-Minute, Easy-To-Use Covid-19 Antigen Test Receives Fda Emergency Use Authorization; Mobile App Displays Test Results To Help Our Return To Daily Life; Ramping Production To 50 Million Tests A Month (Aug. 26, 2020).

* cited by examiner

*Primary Examiner* — Vernal U Brown
(74) *Attorney, Agent, or Firm* — The Concept Law Group, P.A.; Robert C. Kain, Jr.

(57) ABSTRACT

System and methods for infectious disease prevention includes transmitting, via a server, a facility credential associated with a facility configured to identify a user operating on an application deployed by server on a mobile computing device. The server receives a user identification test code (UITC) associated with a status of an infectious disease of the user. The server then generates a two-dimensional code associated with the facility credential based on the UITC. The server determines if the two-dimensional code is valid for permitting access to the facility based on a vaccine indicator confirming that the user has been vaccinated for the infectious disease. Thereafter, the server activates the two-dimensional code on the mobile computing device for a predetermined period of time. A gatekeeper device scans the two-dimensional code from the mobile computing device and then permits the user access to the facility within the predetermined period of time based on the facility credential and the two-dimensional code.

20 Claims, 16 Drawing Sheets

Related U.S. Application Data

(60) Provisional application No. 63/018,823, filed on May 1, 2020.

(51) Int. Cl.
*G16H 10/60* (2018.01)
*G06K 19/06* (2006.01)
*G06K 7/14* (2006.01)
*G07C 9/10* (2020.01)
*H04W 4/029* (2018.01)
*G16H 10/40* (2018.01)
*H04L 29/06* (2006.01)
*H04L 9/08* (2006.01)
*H04W 12/64* (2021.01)
*G07C 9/25* (2020.01)

(52) U.S. Cl.
CPC .............. *G07C 9/10* (2020.01); *G07C 9/257* (2020.01); *G16H 10/40* (2018.01); *G16H 10/60* (2018.01); *H04L 9/0816* (2013.01); *H04L 63/08* (2013.01); *H04W 4/029* (2018.02); *H04W 12/64* (2021.01)

(58) Field of Classification Search
CPC ........ G16H 50/00; G16H 10/40; G16H 10/60; A61B 5/01
See application file for complete search history.

SYSTEMS AND METHODS FOR MANAGING INFECTIOUS DISEASE DISSEMINATION

CROSS-REFERENCE TO RELATED APPLICATION

This is a continuation patent application which claims priority to U.S. patent application Ser. No. 17/112,386, filed Dec. 4, 2020, now pending, and U.S. Provisional Patent Application No. 63/018,823 filed May 1, 2020, the entirety of which is incorporated by reference.

FIELD OF THE INVENTION

The present invention relates generally to disease dissemination prevention, and, more particularly, relates to systems and methods for managing infectious disease dissemination prevention.

BACKGROUND OF THE INVENTION

An instance where an illness and/or disease is widespread over multiple countries and continents is commonly referred to as a pandemic. Pandemics not only cause significant economic, social, and political disruption, but also require drastic modifications to the everyday lives of individuals. For example, SARS-CoV-2 (also know as Covid-19 or Coronavirus) has demanded a significant adjustment to traditional activities that include managing large congregations of people due to not only its inherent contagiousness but also the high mortality rate. For examples, activities such as sporting events, concerts, cruises, and other applicable activities that ordinarily draw large congregations of people have been drastically impacted and/or halted altogether due to the inability to simultaneously practice social distancing and prevent dissemination of the deadly disease. As a result, crucial components of the economy have been impacted dramatically such as the employment rate, venue availability, product demand, and many other aspects of the economy.

Precautionary measures such as social distancing, quarantining, and isolation are common attempts to mitigate the dissemination of the disease; however, a major drawback of these attempts is that they are counterintuitive to the concept of mass congregations. A recent adaptive approach is to virtualize the presence of spectators and audiences during live-streamed events by digitally imposing viewers streaming the events into designated "virtual fan" spots and integrating crowd sound-effects in an attempt to mimic the traditional venue environment. However, this approach not only fails to directly equate to the authentic packed venue environment, but more importantly it fails to address the aforementioned economic factors caused by the disease. Moreover, certain industries, such as concerts and other live performances, are solely dependent on the ability to assemble rendering it difficult to manage disease dissemination within enclosed environments.

Furthermore, preventative disease dissemination strategies such as contact tracing have been integrated into practice in an attempt to trace disease cases back to a carrier. However, these approaches lack the mechanisms necessary to efficiently collect large quantities of data associated with monitoring individuals' whereabouts and actions in addition to determining if an individual has tested positive for the disease within a reasonable timeframe. For example, an individual may be tested for the disease requiring at least 48 hours to receive the results of the test due to testing center logistics only for the individual to come into contact with numerous other individuals during this period of uncertainty.

Therefore, a need exists to overcome the problems with the prior art as discussed above. In particular, what is needed is a system and method to not only accurately test and monitor individuals, but also control access permissions of said individuals into venues and workspaces based on the result of their test.

SUMMARY OF THE INVENTION

The invention provides a system and method for infectious disease prevention that overcomes the hereinaforementioned disadvantages of the heretofore-known devices and methods of this general type and that effectively prevents dissemination of infectious diseases; in particular, in environments that warrant mass congregations of individuals such as sporting events, live performances, festivals, employer sites, or any other applicable venue possible for exposure to infectious diseases.

With the foregoing and other objects in view, there is provided, in accordance with the invention, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a method for infectious disease prevention. The method also includes transmitting, via a server, a facility credential associated with a facility configured to identify a user operating on an application deployed by the server from a mobile computing device; receiving, via the server, a user identification test code (UITC) associated with a status of an infectious disease of the user; generating, via the server, a two-dimensional code associated with the facility credential based on the UITC; determining, via the server, if the two-dimensional code is valid for permitting access to the facility based on the status of the infectious disease; activating, via the server, the two-dimensional code on the mobile computing device for a predetermined period of time; reading, via a gatekeeper device, the two-dimensional code on the mobile computing device; and permitting, via the gatekeeper device, the user access to the facility within the predetermined period of time based on the facility credential and the two-dimensional code. Other embodiments of this aspect include corresponding computer systems, apparatus, and computer programs recorded on one or more computer storage devices, each configured to perform the actions of the methods.

In accordance with another feature, an embodiment of the present invention includes a method for infectious disease prevention may include: monitoring, via the server or the gatekeeper device, a plurality of activities of the mobile computing device associated with the user relative to the facility. The method for infectious disease prevention may include: scanning, via an infectious disease testing module, an unloaded infectious disease test kit at a testing site with the uitc associated with the user; and receiving, via the infectious disease testing module, the status of the infectious disease based on a loaded infectious disease test kit associated with the uitc. The method for infectious disease prevention may include: receiving, via the infectious disease testing module, a topical form of identification associated with the user; verifying, via the infectious disease testing module, the topical form of identification associated with the user; and transmitting, via the infectious disease testing module, the uitc to the server. Verifying the topical form of identification associated with the user may include: comparing, via the infectious disease testing module, the topical form of identification to a primary source of identification on the mobile computing device. The testing site is proximate to the facility. The method for infectious disease prevention may include: tracking, via the server or the gatekeeper device, the geographic location of the mobile computing device. The method for infectious disease prevention may include: receiving, via the server or the gatekeeper device, a plurality of geo-tracking data from the mobile computing device over a communication network. The method for infectious disease prevention may include: defining, via the server or the gatekeeper device, at least one geofence based on a geographic proximity relative to the facility. The method for infectious disease prevention may include: deactivating, via the server or the gatekeeper device, the two-dimensional code based upon the server or gatekeeper device detecting the mobile computing device outside of the at least one geofence. The method for infectious disease prevention may include: deactivating, via the server or the gatekeeper device, the two-dimensional code based upon the server or the gatekeeper device detecting the mobile computing device outside of the at least one geofence for a predetermined period of roaming. The facility credential is an identification mechanism unique to the user and the mobile computing device. Implementations of the described techniques may include hardware, a method or process, or computer software on a computer-accessible medium.

In accordance with a further feature of the present invention, a system for infectious disease prevention a server deploying an application designed and configured for: transmitting a facility credential associated with a facility configured to identify a user operating on the application from a mobile computing device; receiving, via the server, a user identification test code (uitc) associated with a status of an infectious disease of the user; generating a two-dimensional code associated with the facility credential based on the uitc; determining, based on the uitc, if the two-dimensional code is valid for permitting access to the facility; activating the two-dimensional code for a predetermined period of time; a gatekeeper device designed and configured for: reading the two-dimensional code on the mobile computing device; and permitting the user access to the facility within the predetermined period of time based on the facility credential and the two-dimensional code. Other embodiments of this aspect include corresponding computer systems, apparatus, and computer programs recorded on one or more computer storage devices, each configured to perform the actions of the methods.

In accordance with a further feature of the present invention, the system for infectious disease prevention where the server or the gatekeeper device is further designed and configured for: monitoring a plurality of activities of the mobile computing device associated with the user relative to the facility. The server or the gatekeeper device is further designed and configured for: monitoring a plurality of activities associated with the user relative to the facility. The system for infectious disease prevention may include an infectious disease testing module designed and configured for: scanning an unloaded infectious disease test kit at a testing site with the uitc associated with the user; and receiving the status of the infectious disease based on a loaded infectious disease test kit associated with the uitc. The server or gatekeeper device is further designed and configured for: tracking the geographic location of the mobile computing device. The server or gatekeeper device is further designed and configured for: receiving a plurality of geo-tracking data from the mobile computing device over a communication network. The server or gatekeeper device is further designed and configured for: defining at least one geofence based on a geographic proximity relative to the facility. The server is further designed and configured for: deactivating the two-dimensional code based upon the server or gatekeeper device detecting the mobile computing device outside of the at least one geofence. The server is further designed and configured for: deactivating the two-dimensional code based upon the server or the gatekeeper device detecting the mobile computing device outside of the at least one geofence for a predetermined period of roaming. The facility credential is an identification mechanism unique to the user and the mobile computing device. Verifying the topical form of identification associated with the user may include: comparing, via the infectious disease testing module, the topical form of identification to a primary source of identification on the mobile computing device.

In accordance with the present invention, a system for infectious disease prevention an infectious disease testing module designed and configured for: scanning an unloaded infectious disease test kit at a testing site with a user id test code (uitc) associated with a user, receiving a status of an infectious disease of the user based on a loaded infectious disease test kit. The system also includes a server deploying an application designed and configured for: transmitting a facility credential associated with a facility configured to identify the user operating on the application from a mobile computing device, receiving an indication that the user is present at the testing site, receiving the uitc may include the status of the infectious disease based on the indication, generating a two-dimensional code associated with the facility credential based on the uitc, activating the two-dimensional code for a predetermined period of time. The system also includes a gatekeeper device designed and configured for: reading the two-dimensional code on the computing device, and permitting the user access to the facility within the predetermined period of time based on the facility credential and uitc. Other embodiments of this aspect include corresponding computer systems, apparatus, and computer programs recorded on one or more computer storage devices, each configured to perform the actions of the methods.

In accordance with another feature, an embodiment of the present invention also includes the system for infectious disease prevention where activating the two-dimensional code for a predetermined period of time may include: determining, via the server, the two-dimensional code is valid for permitting the user access to the facility based on the user identification code indicating a negative status of the infectious disease. The infectious disease testing module is further designed and configured for: receiving a topical form of identification associated with the user; verifying the topical form of identification associated with the user; and transmitting the uitc to the server. The server or gatekeeper device is further designed and configured for: defining at least one geofence based on a geographic proximity relative to the facility. The testing site is proximate to the at least one geofence. The server is further designed and configured for: deactivating the two-dimensional code based upon the server or gatekeeper device detecting the mobile computing device outside of the at least one geofence. The server is further designed and configured for: deactivating the two-dimensional code based upon the server or the gatekeeper device detecting the mobile computing device outside of the at least one geofence for a predetermined period of roaming. The system for infectious disease prevention may include: a user personal profile (upp) module designed and configured for: receiving a plurality of user data associated with the user from the server; generating a upp id code based on the plurality of user data; and linking the upp id code with the uitc may include the status of the infectious disease.

In accordance with yet another feature, an embodiment of the present invention includes the method also includes transmitting, via a server, to a mobile computing device, an employer facility credential associated with an employer facility configured to identify an employee. The method also includes transmitting, via the server, at least a topical identification associated with the employee; receiving, via the server, a user identification test code (uitc) associated with a status of an infectious disease of the employee; generating, via the server, a two-dimensional code associated with the employer facility credential based on the uitc. The method also includes activating, via the server, the two-dimensional code based on determining the two-dimensional code is valid for permitting access to the facility. The method also includes reading, via a gatekeeper device, the employer facility credential on the mobile computing device; and permitting, via the gatekeeper device, the employer access to the facility based on the employer facility credential and the two-dimensional code.

In accordance with a further feature of the present invention, the method for employee infectious disease prevention may include: scanning, via an infectious disease testing module, an unloaded infectious disease test kit at a testing site; scanning, via the infectious disease testing module, an unloaded infectious disease test kit at a testing site; The method for employee infectious disease prevention may include: tracking, via the server, the geographic location of the mobile computing device. The method for employee infectious disease prevention may include: defining, via the server or the gatekeeper device, at least one geofence based on a geographic proximity relative to the facility. The method for employee infectious disease prevention may include: deactivating, via the server or the gatekeeper device, the two-dimensional code based upon the server or gatekeeper device detecting the mobile computing device outside of the at least one geofence. The method for employee infectious disease prevention may include: deactivating, via the server or the gatekeeper device, the two-dimensional code based upon the server or the gatekeeper device detecting the mobile computing device outside of the at least one geofence for a predetermined period of roaming. The employer facility credential is an identification mechanism unique to the employee and the mobile computing device. The testing site is proximate to the employer facility. The method for employee infectious disease prevention may include: monitoring, via the server or the gatekeeper device, a plurality of activities associated with the employee relative to the employer facility.

In accordance with a further feature of the present invention, the method also includes transmitting, via a server, a facility credential associated with a facility configured to identify a user operating on an application deployed by the server; receiving, via the server, a user identification test code (uitc) associated with a status of an infectious disease of the user; generating a two-dimensional code configured to be associated with the facility credential based on the uitc; activating, via the server, the two-dimensional code on a substrate for a predetermined period of time; reading, via a gatekeeper device, the two-dimensional code from the substrate; and permitting, via the gatekeeper device, the user access to the facility within the predetermined period of time based on the facility credential and the two-dimensional code.

Although the invention is illustrated and described herein as embodied in a system and methods for managing infectious disease dissemination, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system. Those skilled in the art can understand the specific meanings of the above-mentioned terms in the embodiments of the present invention according to the specific circumstances.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

Regarding FIGS. 9-16.

DETAILED DESCRIPTION

Figure 1:
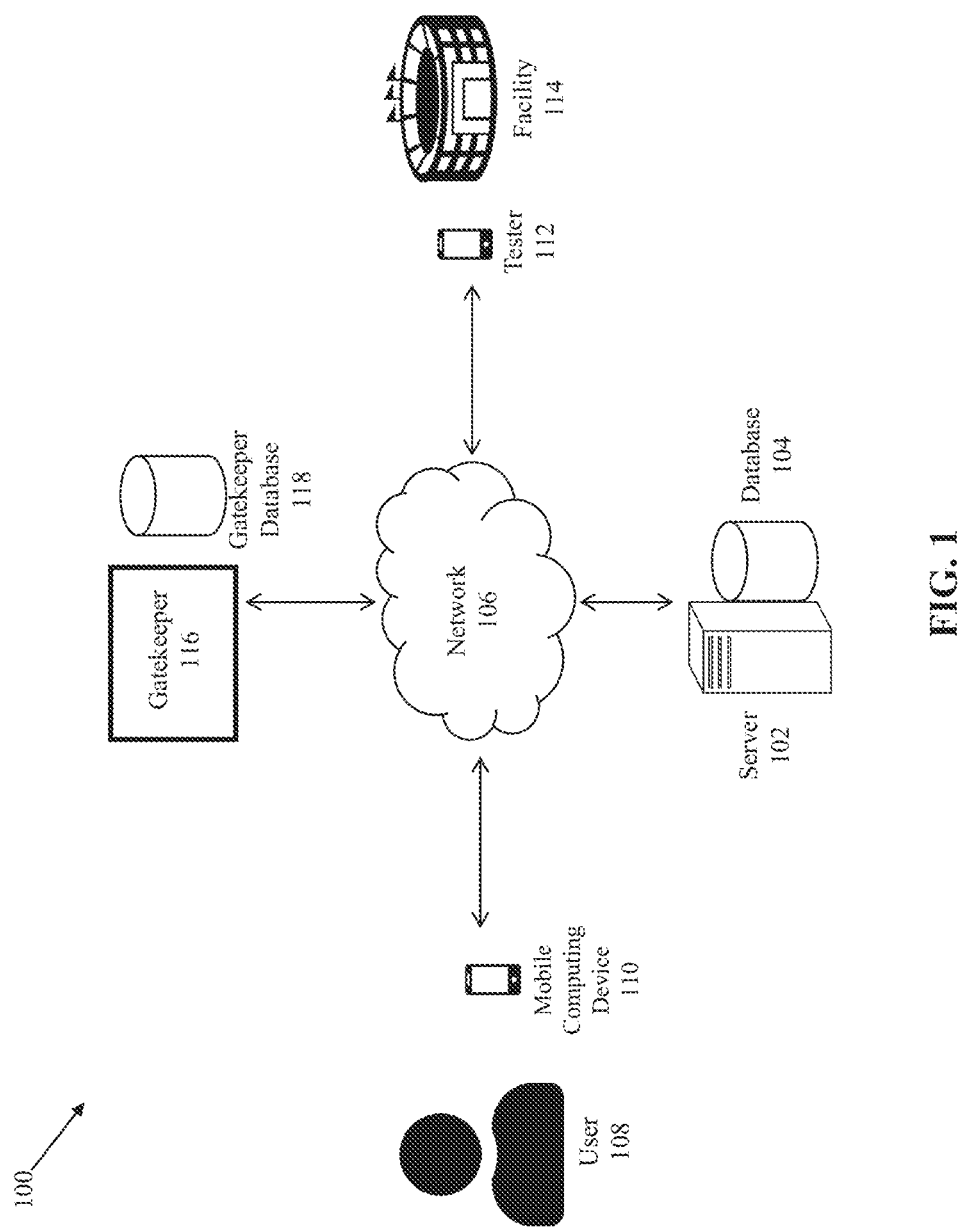
FIG. 1 is a block diagram depicting an exemplary system for infectious disease prevention, according to an example embodiment.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient system of infectious disease prevention configured to prevent individuals from exposure to infectious diseases in mass-gathering environments along with ensure that individuals that are infectious disease negative, have infectious disease anti-bodies, and/or have received infectious disease vaccinations are able to enter mass-gathering environments in a secure manner. Embodiments of the invention provide a mobile application (or a series of communicatively coupled mobile applications) provided via a server, a gatekeeper device, and an infectious disease testing module each of which are communicatively coupled in order to provide the system of infectious disease prevention. In addition, embodiments of the invention provide a method of infectious disease prevention configured to manage and harmonize processes associated with managing dissemination of infectious diseases. The systems and methods described herein are configured to monitor users and create controlled environments for said users by generating venue-specific and user-specific credentials associated with on-site generated test results configured to provide access to a given venue. The system is further configured to establish a geo-fence associated with the venue specific credentials to track and monitor activities of the user in order to prevent exposure to an infectious disease along with reduce potential dissemination of the infectious disease.

Referring now to FIG. 1, a system for infectious disease prevention 100 is depicted according to an exemplary embodiment. In one embodiment, system 100 includes a server 102, a database 104, a communications network 106, a user 108, a mobile computing device 110 associated with user 108, a testing computing device 112 associated with a facility/venue 114, and a gatekeeper device 116. System 100 is a computer-based system and the various components of system 100 are implemented at least partially by hardware at one or more computing devices, such as one or more hardware processors executing instructions stored in one or more memories for performing various functions described herein. For example, descriptions of various components (or modules) as described in this application may be interpreted by one of skill in the art as providing pseudocode, an informal high-level description of one or more computer structures. System 100 illustrates one of many possible arrangements of components configured to perform the functionality described herein. FIG. 1 shows several advantageous features of the present invention, but, as will be described below, the invention can be provided in several shapes, sizes, combinations of features and components, and varying numbers and functions of the components. Other arrangements may include fewer or different components, and the division of work between the components may vary depending on the arrangement. In particular, server 102 may be a local and/or cloud server configured to allocate or assign tasks inherent to server 102 to any applicable component or module of system 100. For example, server 102 may utilize and/or coordinate with gatekeeper device 116 in order to manage access permissions of user 108 to facility 114 in addition to performing monitoring of actions of user 108 within and proximate to facility 114 in order to determine if user 108 has been exposed or at risk to being exposed to an infectious disease.

In one embodiment, server 102 receives and transmits data from mobile computing device 110 over network 106 allowing user 108 to interact with server 102 via one or more graphical user interfaces presented on mobile computing device 110; thus, server 102 is configured to deploy an application on mobile computing device 110 designed and configured to operate as a centralized platform for user 108 to transmit and/or receive data relating to system 100. In one embodiment the centralized platform deployed by server 102 may be a plurality of platforms associated with system 100, wherein each platform of the plurality of platforms serves a specific function within system 100. For example, a first application may be used to generate and present the admissions mechanism to user 108, a second application may be used by testing computing device 112 to administer and protect (via encryption and other applicable security mechanisms) testing and testing credentials associated with an infectious disease testing site in relation to user 108, a third application may be utilized by gatekeeper device 116 to monitor aspects of system 100 associated with facility 114 in order to ensure that each user of system 100 includes a unique admissions mechanism for entry into facility 114, and a fourth application may be an overall infrastructure administrative software configured to provide venue specific functionality for facility 114. It is to be understood that although user 108 is referring to a patron at one or more events associated with facility 114, system 100 further supports utilization of the aforementioned applications based on the applicable entity and their purpose within system 100. For example, the first application is preferably applied to user 108 operating on mobile computing device 110 who is receiving testing for an infectious disease and being admitted to facility 114 based on results of said testing, the second application is preferably applied to staff associated with a testing center, operating on testing computing device 112, processing one or more biological samples of user 108 for a status of an infectious disease, the third application is preferably applied to staff associated with facility 114 to manage entry and activities of user 108 within facility 114, the fourth application is preferably applied to an administrator configuring the details associated with system 100 relating specifically to facility 114, such as but not limited to, event ticket allocation, permissions configuration, and any other applicable type of administrative functions to operate system 100.

Server 102 may solicit data from user 108 and generate and subsequently store non-confidential user information associated with user 108 in database 104 in real time. In one embodiment, server 102 may continuously update database 104 with new or supplemental data associated with user 108 acquired from one or more components of system 100. For example, server 102 may continuously receive various forms of sensor data from one or more wireless sensor networks of a sensor module (described in greater detail in reference to FIG. 3) and store the applicable sensor data to a user record associated with user 108 on database 104.

As described herein, a facility/venue 114 may be a stadium, arena, sports complex, concert hall, amphitheater, banquet hall, employer premises/workplace, hotel/resort, cruise, casino, convention center, theme park, airport, public transportation station, school/university, hospital, assisted care facility, or any other locale configured to retain a congregation of individuals. As described herein, mobile computing device 110 and any other applicable computing device of system 100 includes but is not limited to a mobile phone, tablet, smart phone, desktop, laptop, wearable technology, or any other applicable device or system including at least a processor.

In one embodiment, gatekeeper device 116 includes a radio-frequency identification (RFID) and/or two-dimensional code scanner component configured to directly scan tagging identification mechanisms associated with identifying a status of an infectious disease associated with user 108 or admissions mechanisms relating to entry of user 108 into facility 114. Gatekeeper device 116 may be a network of gatekeeper devices communicatively coupled and distributed throughout facility 114 resulting in a specific gatekeeper device to serve as an entrance gatekeeper device and the remaining gatekeeper devices to function as checkpoints to enter into designated areas within or proximate to facility 114. It is to be understood that gatekeeper device 116 functions as the entity configured to control access or denial of entry of user 108 into facility 114 or proximate to facility 114 based on encrypted admission mechanisms specific to user 108 in order to ensure that user 108 is in fact who they proclaim to be and that the admissions mechanism are not a copy of an admissions mechanism intended for another user. In one embodiment, gatekeeper device 116 further includes a gatekeeper database 118 configured to serve as a repository for information suitable to authenticate user 108 for entry into facility 114. Gatekeeper device 116 may receive data from server 102 or an applicable module internal or external to system 100 in order to efficiently read/scan admissions mechanisms and subsequently permit user 108 into facility 114 based on the admissions mechanisms.

In one embodiment, server 102 is further configured to collect, analyze, and transmit one or more datasets either collected from one or more modules associated with system 100 or generated by server 102. For example, server 102 may collect one or more datasets associated with user 108, via mobile computing device 110 and/or the one or more modules associated with system 100, and perform one or more analyses based on the collected datasets in order to determine a score relating to an infectious disease risk of user 108 or probability of contracting and/or disseminating the infectious disease. Datasets associated with user 108 may include, but are not limited to, personal user data (name, age, contact information, etc.), biological sample specific data, topical identification information, and any other applicable user-specific data configured to be stored in database 104. Datasets associated with user 108 are configured to be stored to an external database associated with an entity external to system 100 to ensure that confidential personal data is not stored within system 100. System 100 may by used as a porting mechanism to collect and transfer the datasets associated with user 108 to the external database. In one embodiment, server 102 communicates data generated by at least one of mobile computing device 110, testing computing device 112, gatekeeper device 116, or any other applicable third party configured to be associated with system 100. For example, an event may be hosted at facility 114; however, a ticket sales and distribution company separate from system 100 may be configured to provide necessary data associated with the facility credential utilized by user 108 in order to be provided entry into facility 114.

It is to be understood that server 102 is configured to function as the foundational component of system 100 allowing information to be collected and transmitted to applicable entities based on its purpose in respect to facility 114 and/or one or more events associated with facility 114. It is to be understood that the one or more events associated with facility 114 may occur over various periods of time which directly impacts a predetermined period of time decided by server 102 in which a two-dimensional code (described in greater detail in FIG. 2B) is generated and activated by server 102 in order for user 108 to be eligible to access facility 114. For example, the one or more events associated with facility 114 may span across multiple days in which server 102 may determine that the predetermined period of time corresponds to the timing and length of the one or more events.

Figure 2B:
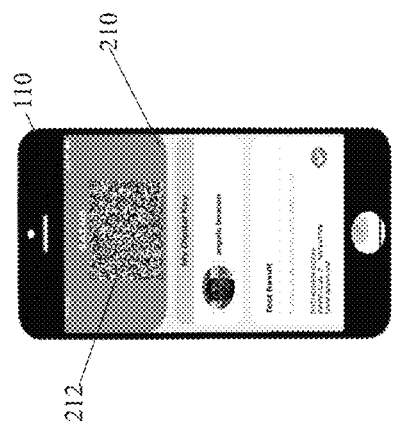
FIGS. 2A-B are block diagrams depicting an exemplary geofencing component and facility admission credential associated with the system for infectious disease prevention, according to an example embodiment.
Figure 2A:
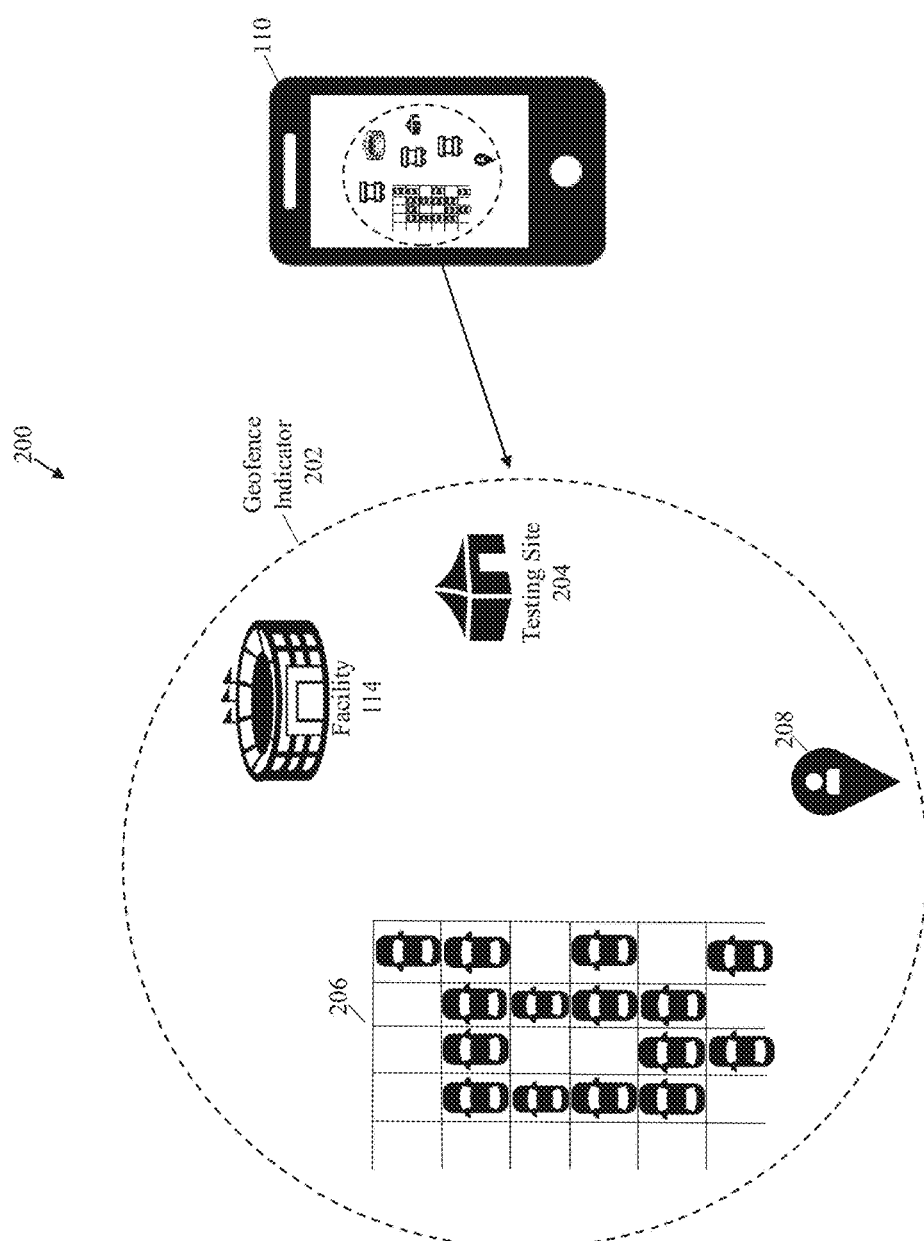

Referring now to FIGS. 2A-B, a geofencing component 200 provided within an operating environment for system 100 is depicted according to an exemplary embodiment. In one embodiment, geofencing component 200 includes a geofence indicator 202 configured to be allocated by server 102 and/or gatekeeper device 116 based on facility 114. It is to be understood that geofence indicator 202 is configured to serve as a definition of a plurality of geographic designators associated with facility 114 in order to function as a virtual boundary for user 108. In one embodiment, geofence indicator 202 virtually encloses facility 114, a testing site 204 proximate to facility 114, and the plurality of geographic designators associated with facility 114 which includes but is not limited to parking lots 206, parking garages, vendors, kiosks, promotional booths, or any other applicable entity within reasonable range of facility 114 that is within the territory of geofence indicator 202.

In one embodiment, testing site 204 is configured to allow user 108 to receive testing for an infectious disease prior to user 108 receiving at least a two-dimensional code 212 from server 102 via mobile computing device 110. It is to be understood that testing site 204 is configured to function as a rapid screening site of infectious diseases configured to receive (digitally or physically) one or more biological samples associated with user 108, and perform real-time testing of the one or more biological samples (on-site or remote) in order to generate a status of an infectious disease associated with user 108 based on the one or more biological samples. The receiving of the one or more biological samples may be accomplished by a disease testing proctor associated with testing site 204. Examples of collecting one or more biological samples of user 108 may include, but is not limited to, nasal swab, throat swab, drawing blood, saliva analysis, digital image analysis, or any other applicable form of receiving biological samples for biological based testing. The real-time testing of the one or more biological samples may be accomplished by, but not limited to, polymerase chain reaction (PCR) testing, antigen testing, antibody testing, vaccine testing, or any other applicable form of testing suitable for detecting the status of a biological diagnosis. The operations associated with testing site 204 in addition to the generation of two-dimensional code 212 based on the status of an infectious disease will be discussed in greater detail in reference to FIG. 4.

A current user position 208 is utilized by geofencing component 200 in order to accurately depict the current location of user 108 relative to facility 114 on a digital map or geographic information system (GIS), such as a global positioning system (GPS) or global navigation satellite system (GNSS), configured to be displayed to user 108 via a mapping graphical user interface presented on mobile computing device 110. In one embodiment, geofence indicator 202 is defined by server 102 based on the geographic location of facility 114 and the proximity of the plurality of geographic designators relative to facility 114 wherein the location of facility 114, the plurality of geographic designators, and the current user position 208 are configured to be viewed by user 108 and updated in real-time on the mapping graphical user interface depicting an interactive 2D map or 3D map showing the boundaries of geofence indicator 202. In addition, server 102 and/or gatekeeper device 116 are configured to receive a plurality of geo-tracking data from mobile computing device 110 over network 106 in order for server 102 to monitor navigational factors associated with user 108, such as but not limited to, orientation, angular rate, specific force, or any other applicable inertial measurement data, and update the mapping graphical user interface in real-time based on the navigational factors. It is to be understood that one of the core purposes of geofencing component 200 is to ensure that user 108 does not roam far way from facility 114 while waiting for test results or in between events at facility 114 increasing the probability of exposure to an infectious disease. In one embodiment, server 102 transmits a notification to mobile computing device 110 alerting user 108 that they are near the virtual boundary imposed by geofence indicator 202 when server 102 detects current user position 208 proximate to the virtual boundary. In one embodiment, server 102 deactivates two-dimensional code 212 upon server 102 and/or gatekeeper device 116 detecting via the collected geo-tracking data and positioning of current user position 208 that user 108 is outside of the virtual boundary.

Server 102 is configured to transmit a facility credential 210 specific to facility 114 and a two-dimensional code 212 specific to user 108 and/or mobile computing device 110 once server 102 and/or gatekeeper device 116 detects mobile computing device 110 within the virtual boundary of geofence indicator 202. It is to be understood that facility credential 210 is an applicable endorsement mechanism configured to certify that user 108 is who they proclaim to be and qualified to enter into facility 114 based upon negative test results for an infectious disease. Facility credential 210 may be a virtual badge, near field communication (NFC) tag, QR code, or any other applicable form of security digital identification configured to serve as a digital ticket/access mechanism specific to user 108 to enter into facility 114. In one embodiment, facility credential 210 may be manifested via a substrate, such as a hardcopy configured to include substance scannable by gatekeeper device 116. Two-dimensional code 212 may be a bar code, data matrix code, QR code, or other machine readable unique identification code configured to be scannable. In a preferred embodiment, server 102 transmits facility credential 210 and/or two-dimensional code 212 to a graphical user interface presented on mobile computing device 110, as illustrated in FIG. 2B, via the application deployed by server 102. Server 102 activates two-dimensional code 212 for the predetermined period of time ensuring that user 108 enters into facility 114 subject to the specific details associated with both facility 114 and the one or more events associated with facility 114. For example, facility 114 may be a sports complex hosting a tennis tournament with multiple events occurring over various times throughout the course of a given ticket-specific timeframe (10 am to 3 pm allocated on Tuesday through Thursday of a particular week) in which user 108 may be entitled to access particular events within the timeframe based on the type of ticket purchased. Thus, server 102 is configured to deactivate two-dimensional code 212 during 3:01 pm to 9:45 am of the particular week. In the same sports complex example, the multiple events may be occurring on various tennis courts throughout the course of a given timeframe in which user 108 only has access to particular events hosted on particular tennis courts and does not have access to any other events hosted on any other tennis courts based on the type of ticket purchased. Thus, server 102 is configured to define geofence indicator 202 to exclude or not encompass the other tennis courts hosting the unpermitted event resulting in server 102 deactivating two-dimensional code 212 upon detecting user 108 attempting, via an attempted scan by gatekeeper device 116, to enter the unpermitted event. In addition, server 102 is further configured to deactivate two-dimensional code 212 if two-dimensional code 212 is not scanned by gatekeeper device 116 or if current user position 208 is not detected proximate or within facility 114 for a substantial portion of the predetermined period of time.

In one embodiment, geofencing component 200 may include a plurality of geofence indicators 202 in which facility credential 210 includes a different functionality for each one of the geofence indicators and wherein each one of the geofence indicators includes a rule configured to be enforced within the respective geofence indicator. For example, the event hosted at facility 114 may be a music festival configured to include various tiers of permissions based on the type of ticket purchased by user 108 (VIP, general admission, deluxe package, etc.). In other words, a first geofence indicator may include a first tier wherein user 108 has a first set of permissions and when server 102 detects current user position 208 within a second geofence indicator including a second tier reflecting a second set of permissions then server 102 either updates two-dimensional code 212 or provides a new two-dimensional code 212 to mobile computing device 110 altogether wherein both sets of permissions are directly correlated to the applicable tier. In one embodiment, the new or updated two-dimensional code 212 generation and transmission performed by server 102 is triggered by gatekeeper device 116 scanning the original two-dimensional code 212. In one embodiment, facility credential 210 and two-dimensional code 212 may be linked or integrated in which one component may not function without the other; thus, preventing access to facility 114 once facility credential 210 and/or two-dimensional code 212 is scanned by gatekeeper device 116. For example, scanning of two-dimensional code 212 may indicate that the user 108 has a negative status associated with the infectious disease; however server 102 is configured to detect if the user associated with facility credential 210 and the user associated with two-dimensional code 212 match, and if any of the aforementioned do not match then server 102 deactivates facility credential 210 and/or two-dimensional code 212.

Figure 3:
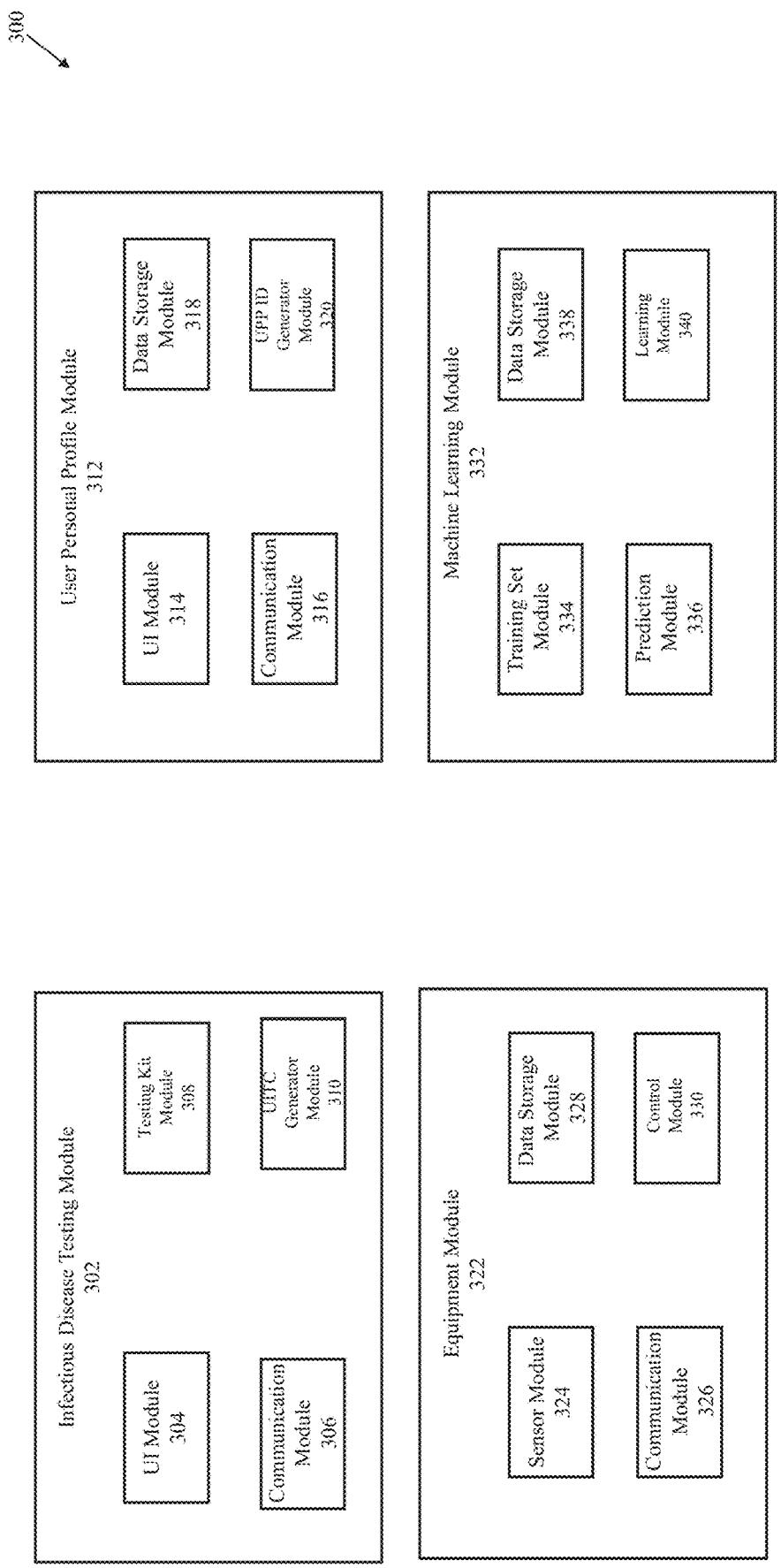
FIG. 3 is a block diagram depicting various modules of the system for infectious disease prevention, according to an example embodiment.

Referring now to FIG. 3, a plurality of modules 300 of system 100 is depicted according to an exemplary embodiment. In one embodiment, the plurality of modules includes an infectious disease testing (IDT) module 302 including a user interface (UI) module 304, an IDT communication module 306, a testing kit module 308, and a user identification test code generator module 310 configured to generate a user identification test code (UITC). The plurality of modules further includes a user personal profile (UPP) module 312, a UPP user interface module 314, a UPP communication module 316, a data storage module 318, a UPP ID generator module 320. The plurality of modules further includes an equipment module 322 including a sensor module 324, an equipment communication module 326, an equipment data storage module 328, and a control module 330. In one embodiment, equipment module 322 includes an infectious disease test kit scanner configured to be associated with infectious disease test kit 302 for the purpose of scanning infectious disease testing kits (unloaded and/or loaded). The plurality of modules further includes a machine learning module 332 including a training set module 334, a prediction module 336, a data storage module 338, and a learning module 340.

It is to be understood that IDT module 302 is associated with testing site 204 and configured to execute the testing for an infectious disease associated with user 108 at testing site 204. In one embodiment, infectious disease testing module 302 may utilize testing kit module 308 to generate infectious disease testing kit two-dimensional codes specific to the infectious disease kit associated with a user that may be transmitted to mobile computing device 110 or solely managed by testing kit module 308, wherein the testing kit two-dimensional code is ultimately related to the status of the infectious disease and is configured to be scanned prior to and after the loading of the biological sample in the infectious disease kit facilitating tracing of the infectious disease kit and the transmission of data relating to the status of the infectious disease to server 102. In one embodiment, infectious disease testing module 302 further includes a timer mechanism configured to alert testing computing device 112 of a first time to have the testing kit two-dimensional code scanned prior and/or concurrent to the biological sample being collected (forming a loaded infectious disease testing kit) and a second time to have the testing kit two-dimensional code scanned once rapid testing of the biological sample is performed, wherein the time period associated with the first and second time is subject to the amount of time the biological sample is completely processed by infectious disease testing module 302. In one embodiment, generation and maintenance of the user's infectious disease status may include the testing kit two-dimensional code indicating whether user 108 received a vaccine in which said information allows infectious disease testing module 302 to filter generation of the two-dimensional code.

As an example of the testing process in one embodiment, after user 108 sets up their profile with server 102, which includes a selfie of user 108, server 102 generates a two-dimensional code (for example, a QR code), to be displayed on mobile computing device 110. When user 108 approaches the proctor at testing site 204, user 108 displays the QR code on the applicable mobile application on mobile computing device 110 and displays the selfie stored on mobile computing device 110. The proctor views the assigned QR code and the selfie and visually confirms that user 108, is present at the test site, and is the authorized user for the system-generated user QR code. The proctor then scans the QR code, wherein the scan is logged into the system. For example, a scan with the proctor's mobile computing device (the proctor's device being earlier logged into the system. The proctor then scans a unique test kit two-dimensional code from the unloaded test kit. In one embodiment, this unique test kit two-dimensional code is earlier printed and is attached and/or imprinted as a sticker to the unloaded test kit. After logging in the test kit two-dimensional code and the user's assigned QR code, the proctor gathers the biological sample from user 108 and places the biological sample on the test kit (then a loaded test kit). In one embodiment, once the test kit is logged into the system, a timer is started (for example 15 minutes) which alerts the back-office testing center or applicable party associated with testing site 204 to check the infectious disease status of the biologic sample on the loaded test kit. Personnel at the test site reports back the status (Y/N) within the pre-set time frame or within a pre-set follow-on time frame back to the system. Once the result is manifested, the back-office test personnel scans the loaded test kit QR code which is forwarded to the system (transmitting the result). After the user's time clocks out (generally a pre-set period after the 15 minute test period), user 108 accesses status via mobile computing device 110, logs into the system, and then either obtains facility credential 210 or not, based upon the status of the infectious disease.

In one embodiment, IDT module 302 is designed and configured to utilize testing kit module 308 in order to scan an unloaded infectious disease testing kit including at least the UITC via testing computing device 112. The UITC is configured to be a manifestation of data representing a negative or positive status of the infectious disease associated with the one or more biological samples; however, UITC may be a scannable authentication token configured to be created by UITC generator module 310 allowing the generated UITC to function as an infectious disease testing kit specific identifier for the user. It is to be understood that UITC is specifically applied to the infectious disease testing kit and is a source of information for the status of the infectious disease specific to the one or more biological samples obtained from the user. There is no utilization of any personal information collected by server 102 and generation of two-dimensional code utilizing the UITC is performed strictly for the purpose of alerting user 108 and server 102 and/or gatekeeper device 116 of the status of the infectious disease associated with the one or more biological samples. In one embodiment, UITC generator module 310 generates and transmits the UITC to testing kit module 308 allowing the UITC to be linked to the infectious disease testing kit. In one embodiment, the UITC may be manually associated with the unloaded infectious disease test kit via the proctor at testing site 204. It is to be understood that the UITC is a unique ID code specific to the infectious disease testing kit (loaded or unloaded) and is configured to be scanned resulting in an indicator relating to either a negative or positive test result associated with the infectious disease based on the one or more biological samples of the loaded infectious disease testing kit. The one or more biological samples are applied to the unloaded infectious disease testing kit generating a loaded infectious disease testing kit. In one embodiment, the loaded infectious disease testing is processed in real-time in order to determine the status of the loaded infectious disease testing kit based on the one or more biological samples. It is to be understood that in an ideal embodiment, IDT module 302 is configured to perform the testing of the one or more biological samples onsite in testing site 204 and provide the results based on the one or more biological samples onsite; however, in some embodiments IDT module 302 is configured to outsource the testing of the loaded infectious disease testing kit to a third party or system external and agnostic to system 100 and receive the testing results relating to the one or more biological samples included in the loaded infectious disease testing kit. IDT module 302 is further configured to receive the status of the infectious disease from testing kit module 308 in the form of a negative test result or positive test result. IDT communication module 306 is configured to transmit all relevant data to server 102 such as UITC and any other relevant data associated with the status of the infectious disease in order for server 102 to generate two-dimensional code 212. In one embodiment, server 102 may provide a status color indicator integrated with the presentation of two-dimensional code 212 representing the status of the infectious disease relating to user 108, said component is discussed in greater detail in relation to FIG. 6 & FIG. 7. For example, server 102 may utilize UITC to generate two-dimensional code 212 wherein the graphical user interface presenting two-dimensional code 212 includes a green background or undertone based on UITC representing a negative status of the infectious disease based on the loaded infectious disease test kit, and a red background or undertone based on UITC representing a positive status of the infectious disease derived from the loaded infectious disease test kit. In one embodiment, server 102 is configured to perform encryption on two-dimensional code 212 when generating two-dimensional code 212, wherein two-dimensional code 212 is designed to be an encrypted string configured to be processed by gatekeeper device 116 upon scanning two-dimensional code displayed on mobile computing device 110.

In one embodiment, UI module 304 is configured to transmit one or more graphical user interfaces to mobile computing device 110 via server 102 in order to collect supplemental information associated with user 108 necessary for testing kit module 308 to render testing of the one or more biological samples. Examples of supplemental information includes, but is not limited to, user verification data such as a topical form of identification, social media user profile data, or any other data associated with verifying the authenticity of user 108. For example, infectious disease testing module 304 may require verification of user 108 before being able to collect the one or more biological samples and apply the one or more biological samples to the infectious disease testing kit wherein user 108 is prompted for a current image of user 108 (hereinafter referred to as topical form of identification) in order to compare the topical form of identification (ie, photo taken in real time of user 108 or social media image) to a primary source of identification such as a driver's license, passport, or any other established form of user verification. Herein, topical form of identification may include, but is not limited to, a real-time captured form of identification such as a captured image or video, retinal scan, or any other applicable real-time means of identification. It is to be understood that IDT module 302 or an applicable third party verification entity performs the aforementioned verification step in order to ensure that the primary source of identification matches the topical form of identification and that the one or more biological samples are sourced from the user associated with both the primary source of identification and the topical form of identification.

It is to be understood that UPP module 312 is configured to link a UPP identification code generated by UPP ID generator module 320 to the UITC allowing user 108 to receive the status of the infectious disease based on the one or more biological samples as the UITC. UPP module 312 operates based on receiving a plurality of user data associated with user 108 via mobile computing device 110. For example, UPP module 312 may utilize UPP user interface module 314 in order to provide one or more graphical user interfaces specifically for receiving user data from mobile computing device 110. UPP module 312 utilizes communication module 316 to transmit prompts for user data associated with user 108 to server 102 and receive responses to the prompts from the inputs of user 108 in mobile computing device 110, wherein UPP module 312 is configured to generate user personal profiles specific to users of system 100 configured to be stored in data storage module 318 and/or database 104. The plurality of user data may include, but is not limited to user contact information, user preferences, mobile computing device 110 metadata, copies of existing forms of identification of user 108 (driver license, passport picture, social media images associated with user 108), or any other applicable type of information derived from or associated with user 108, which is not stored within system 100 but rather ported to an applicable external party for verification. In one embodiment, UPP module 312 manages a personal profile specific to user 108 in order to ensure non-confidential user information associated with user 108 is integrated into system 100. Server 102 transmits the plurality of user data to UPP module 312, wherein a subset of the plurality of user data is transmitted to the IDT module 302, allowing the disease testing proctor, entity associated with testing site 204, or applicable third party to verify the topical form of identification. For example, UPP module 312 may instruct server 102 to request the primary source of identification associated with user 108 for porting purposes in addition to the topical form of identification via mobile computing device 110 in which user 108 uploads an image of a copy of the primary source of identification and uploads the topical form of identification captured by at least a sensor (i.e., a camera) of mobile computing device 110. UPP module 312 may assist testing site 204 in verification of user 108 by providing IDT module 302 the aforementioned forms of identification in order for IDT module 302 or the infectious disease proctor associated with testing site 204 to compare the topical form of identification uploaded via mobile computing device 110 to the primary source of identification.

Equipment module 322 functions as the centralized computer circuitry associated with one or more equipment components utilized by system 100. For example, equipment module 322 may include a plurality of sensors associated with sensor module 324, wherein the plurality of sensors may include but is not limited to, GPS sensors, non-GPS sensors, micro-electricalmechanical sensors, inertial measurement sensors, spectrum sensors, accelerometers, microphones, gyroscopes, magnetometers, infrared sensors, thermal sensors, image sensors, bioimpedance sensor, photoplethysmography sensor, electrocardiographic sensor, electromyographic sensor, galvin skin response sensor, and any other applicable type of sensor configure to collect a plurality of sensor data. In one embodiment, server 102 utilizes sensor module 324 to collect the plurality of sensor data associated with user 108 within system 100. Sensor module 324 may be the component of system 100 utilized to collect physical data associated with user 100 such as but not limited to positioning data, biological data, and any other applicable type of data associated with the functionality of system 100. Sensor module 324 collects the plurality of sensor data and stores it in data storage module 328. In one embodiment, the plurality of sensors associated with sensor module 324 are allocated among components of system 100 such as facility 114 and the plurality of geographic designators associated with facility 114 allowing sensor module 324 to receive sensor data in real-time associated with user 108 and server 102 to function as the eyes and ears of system 100. In one embodiment, sensor module 324 is configured to support computer visioning via images and videos collected by the plurality of sensors. For example, current user position 208 associated with user 108 is obtainable based on the geographic position of mobile computing device 110 relative to the plurality of geographic designators, along with other various data associated with user 108 within geofence indicator 202 such as current body temperature acquired by the thermal sensors, respiratory frequency acquired by inertial measurement sensors, and coughing rate acquired by the micro-electromechanical sensor. The sensor data collected by sensor module 324 is stored in data storage module 328 and is transmitted from equipment module 322 to server 102 via communication module 326. In one embodiment, control module 330 is designed and configured to ensure that system 100 and its components are operating at optimal capacity. For example, control module 330 may be utilized to establish one or more thresholds or filters relating to sensor data received by sensor module 324 in order to ensure that communication module 326, data storage module 328, and server 102 are not overwhelmed by the continuous collection of sensor data relating to patrons of one or more events associated with facility 114.

Machine learning module 332 is designed and configured to utilize a machine learning model or rule-based model via training data generated by training set module 334 in order for prediction module 336 to generate one or more predictions associated with the status of an infectious disease and/or a scoring representing the probability of testing positive for the infectious disease. It is to be understood that machine learning is the study and construction of algorithms that can learn from, and make predictions on, data. Such algorithms operate by building a model from inputs in order to make data-driven predictions or decisions. Thus, a machine learning technique utilized by machine learning module 332 is configured to generate a statistical that is trained based off of data from training set module 334 and subsequently stored in data storage module 338. In one embodiment, learning module 340 is designed for supervised and unsupervised learning and configured to generate one or more machine learning ensembles that exhibit the highest predictive performances. For example, machine learning module 332 may receive sensor data collected via sensor module 324 or access data stored in data storage module 328 in order to utilize training set module 334 to generate and train a machine-learned model based on the received sensor data. It is to be understood that training set module 334 is configured to extract subsets of data from the sensor data and the plurality of user data from UPP module 312 allowing machine learning module 332 to perform data analytics on the subsets of data in an efficient manner. In one embodiment, a new machine is generated regularly by machine learning module 332, such as every month, week, or other period of time. Thus, the new machine-learned model may replace a previous machine-learned model and newly acquired or changed training data may be used to update the model.

Figure 4:
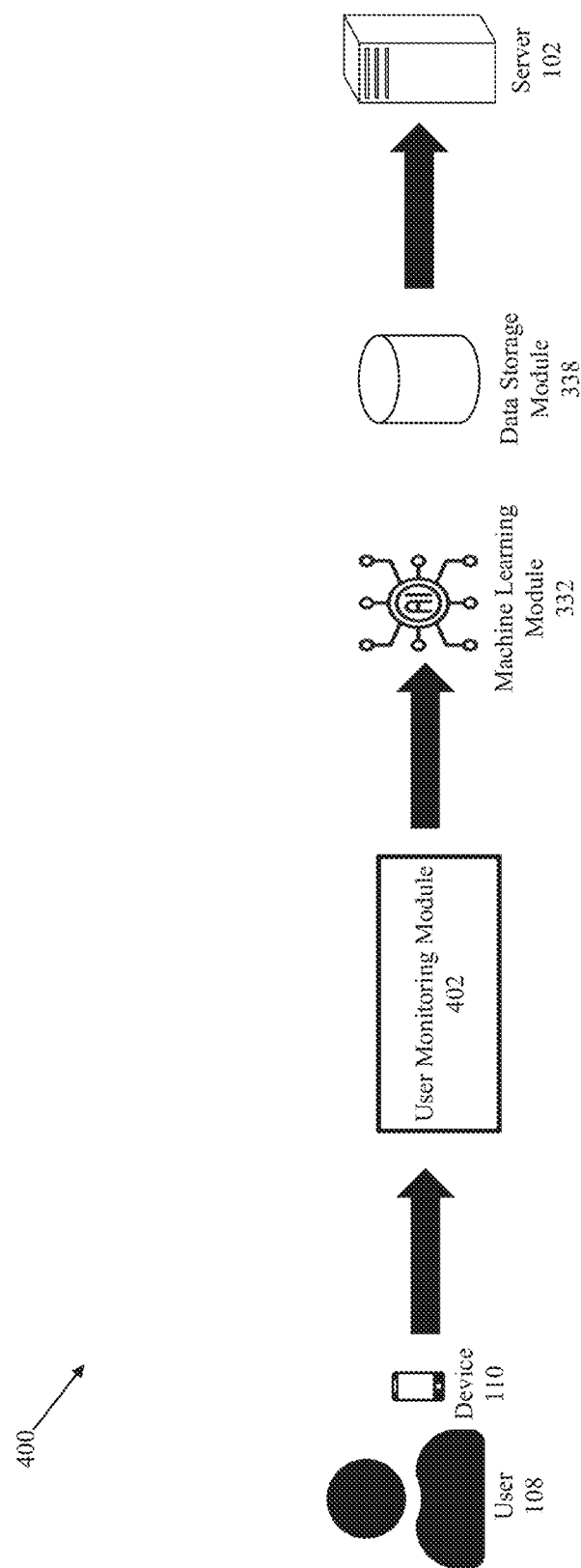
FIG. 4 is an exemplary data flow associated with a user monitoring component of the system for infectious disease prevention, according to an example embodiment.

Referring now to FIG. 4, an exemplary dataflow 400 depicting the aforementioned machine learning components associated with machine learning module 332 is presented, according to an embodiment. In one embodiment, system 100 may further include a user monitoring module 402 configured to be communicatively coupled to server 102, equipment module 322, and machine learning module 332. It is to be understood that user monitoring module 402 is configured to assist server 102 in tracking and monitoring the activities of user 108 within and proximate to facility 114. In one embodiment, user monitoring module 402 is configured to filter data received by sensor module 324 in order to determine if user 108 is performing suspicious activities indicating a high probability of contracting an infectious disease. For example, sensor module 324 may utilize the image sensor, thermal sensor, and micro-electrical mechanical sensor in order for user monitoring module 402 to detect one or more suspicious activities within or proximate to facility 114 such as user 108 not wearing personal protective equipment (mask, gloves, face-shield, etc.), user 108 indicating an abnormally high body temperature, user 108 excessively coughing and/or sneezing, user 108 loitering excessively at or near geofence indicator 202, or any other activities performed by user 108 that would indicate lack of conforming to social distancing and other infectious disease preventative measures. In one embodiment, user monitoring module 402 is configured to receive the user data from server 102 collected directly from mobile computing device 110 allowing user monitoring module 402 to perform one or more analyses based on a plurality of interaction data relating to interactions between user 108 and the plurality of geographic designators associated with facility 114. For example, server 102 is configured to determine the amount of time user 108 is spending at the various geographic designators of the plurality of geographic designators while user 108 is waiting on test results from IDT module 302.

In one embodiment, data and analyses generated by user monitoring module 402 is configured to be transmitted to machine learning module 332 for one or more machine learning techniques to be applied to the data and the resulting data subsequently being stored in data storage module 338 configured to function as a machine learning database. Machine learning module 332 utilizes the one or more predictions generated by prediction module 336 in order to assist learning module 340 with generating at least a scoring reflecting the probability of user 108 testing positive for the infectious disease, wherein the scoring is transmitted to server 102 and subsequently associated with facility credential 210 and/or presented to user 108 via mobile computing device 110. In one embodiment, the scoring may be represented to gatekeeper device 116 via an indicator in which the scoring may be associated with facility credential 210 via server 102 and the indicator is triggered upon scanning or interacting with facility credential 210. For example, one or more gatekeeper monitors operating gatekeeper device 116 may be notified of the scoring via triggering of the indicator which may be a specific color, lighting, sound, or other indicator emitted when gatekeeper device 116 interacts with facility credential 210.

Figure 5:
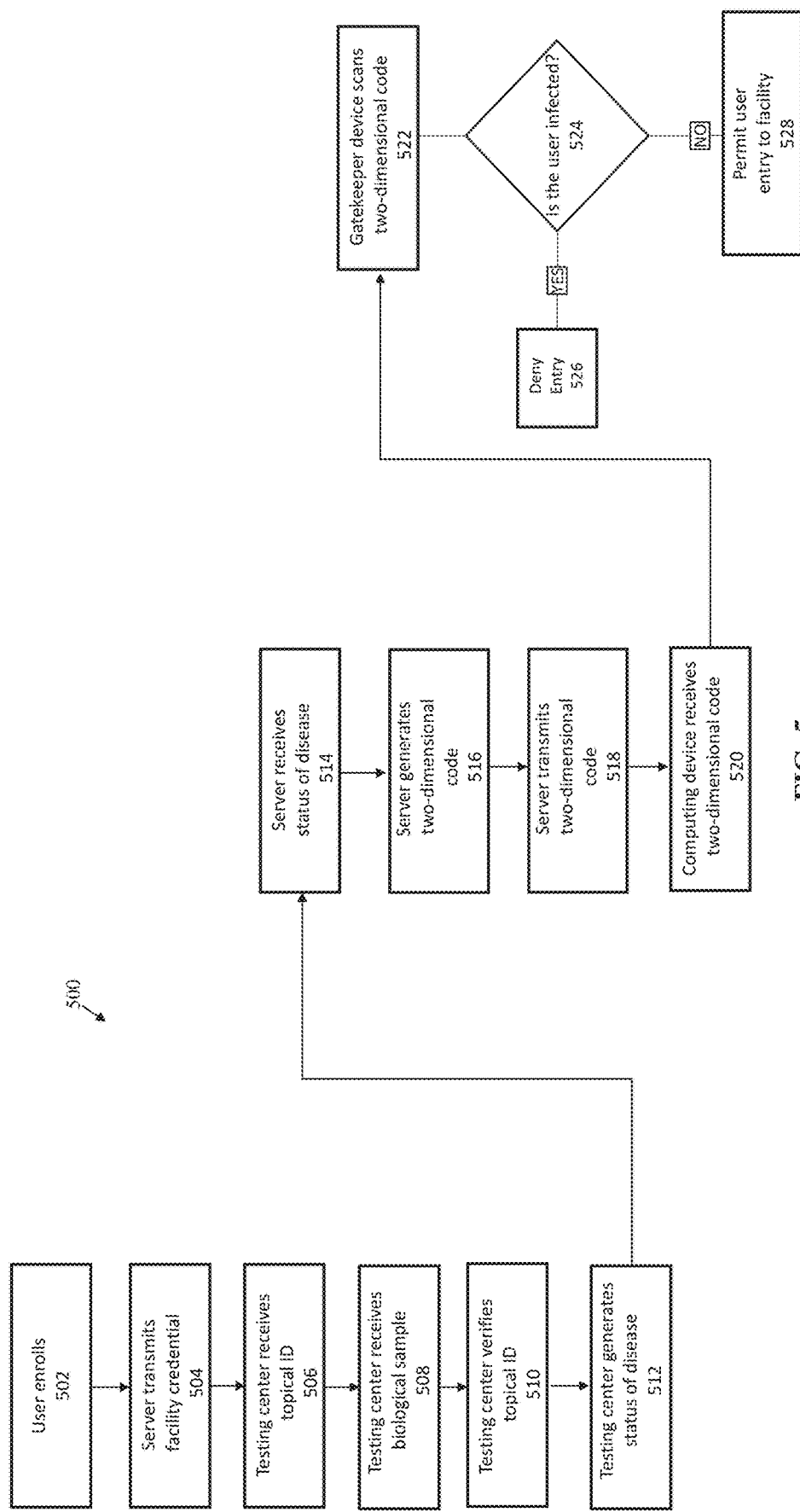
FIG. 5 is a block diagram illustrating an exemplary method for managing infectious disease dissemination, according to an example embodiment.

Referring now to FIG. 5, an exemplary method for managing dissemination of infectious diseases 500 is depicted, according to an example embodiment. At step 502, user 108 enrolls into system 100 by downloading the centralized platform (or the plurality of platforms that make up the centralized platform) over network 106 onto mobile computing device 110 via an application store, such as Google Play store or the Apple App Store and creating the UPP via UPP module 312. It is to be understood that system 100 and the configuration of the centralized platform are configured to merely receive and transmit personal identifiable information such as driver license, email address, or any other confidential information due to the fact that neither server 102 nor any other applicable component of system 100 is configured to store the personal identifiable information because storage of said data could potentially be in violation of HIPAA guidelines. The aforementioned data is configured to be received by system 100 and ported to a third party entity qualified to handle the aforementioned data without violating HIPAA requirements. In one embodiment, user 108 may finalize the UPP by utilizing the camera on mobile computing device 110 to upload topical form of identification to server 102. At step 504, once user 108 is enrolled in the centralized platform, server 102 transmits facility credential 210 to mobile computing device 110; however, it is to be understood that facility credential 210 generated by server 102 and transmitted to mobile computing device 110 once two-dimensional code 212 is generated wherein facility credential is configured to include two-dimensional code 212. In one embodiment, facility credential 210 is transmitted to mobile computing device 110 based on server 102 detecting mobile computing device 110 within a predefined proximity of at least one of facility 114, gatekeeper device 116, geofence indicator 202, and/or the plurality of geographic designators associated with facility 114. The predefined proximity may be based on the perimeter of facility 114. In one embodiment, facility credential 210 may be transmitted to mobile computing device 110 as soon as the applicable event ticket is purchased by user 108; however, it is to be understood that facility credential 210 may not be utilized by user 108 for entry into facility 114 until two-dimensional code 212 is generated. A third party entity may determine based off of user information used to book the particular event at facility 114 that user 108 is eligible to attend the particular event and facility credential 210 may be transmitted to server 102 from the third party entity based on the determination. However, facility credential 210 may not be used solitarily to enter facility 114 due to the fact that user 108 must be tested in order for facility credential 210 to be configured to be scanned and proof of the testing is manifested via the UITC. Prior to or while the UPP is being finalized for user 108, server 102 prompts user 108 for the topical form of identification wherein user 108 may upload a real time identification photo of themselves captured by mobile computing device 110 or may provide a digital copy of a verified form of identification such as a driver's license, passport, or any other applicable verified form of identification. At step 506, testing site 204 receives the topical form identification via IDT module 302. It is to be understood that neither server 102 nor any other component of system 100 store the topical form of identification but rather server 102 ports the topical form identification to IDT module 302 via IDT communication module 306 for the topical form of identification to be utilized by a third party verification entity in order to verify the identity of user 108, and subsequently includes the topical form of identification in the test results by associating the topical form of identification with the UITC. At step 508, testing site 204 receives the one or more biological samples from user 108. The receiving of the one or more biological samples may be performed by a third party testing entity preferably onsite allowing a safe and sanitary collection of blood, saliva, or any other applicable biological sample to be collected from user 108 and tested in real-time. At step 510, testing site 204 may utilize a third party platform (functioning offsite or onsite) to compare the topical form of identification to the primary source of identification. In a preferred embodiment, verification of user 108 is not completed until it is confirmed that all of the topical form of identification, the primary source of identification, and the one or more biological samples are in fact associated with the same individual. During or subsequent to this verification step, the aforementioned loading of the one or more biological samples of user 108 to the unloaded infectious disease testing kit generating a loaded infectious disease testing kit occurs, wherein the disease testing proctor associated with testing site 204 scans, via testing computing device 112, the unloaded infectious disease testing kit including the UITC generated by UITC generator module 310 and loads the unloaded infectious disease testing kit with the one or more biological samples allowing the UITC to be directly correlated to the testing results of the loaded infectious disease testing kit. At step 512, after testing is administered to the one or more biological samples in the loaded infectious disease testing kit, the results of an infectious disease based on the one or more biological samples is generated by testing kit module 308 wherein the results are at least one of a negative result or a positive result for the infectious disease and the results are directly linked and correlated to the UITC.

It is to be understood that the verification, testing, and result generation steps are to be performed in a relatively short amount of time, wherein while the aforementioned steps are taking place system 100 is configured to allow user 108 to freely roam within geofence indicator 202 interacting with the plurality of geographic designators. If server 102 detects current user position 208 roaming too close to the virtual boundary, then server 102 notifies user 108 that user 108 is near the boundary. In one embodiment, server 102 detects current user position 208 outside of the virtual boundary provided by geofence indicator 202 then server 102 notifies user 108 to return to testing site 204 to be retested for the infectious disease. In one embodiment, if server 102 and/or gatekeeper device 116 does not detect that two-dimensional code 212 has been scanned by gatekeeper device 116 within a predetermined amount of time, allocated by server 102, after test results have been generated and two-dimensional code 212 has been generated based on the UITC, then server 102 notifies user 108 that he or she must return to testing site 204 to be tested again. It is to be understood the aforementioned predetermined period of time is determined by server 102 is based on at least one of extractable data associated with facility credential 210, event details of one or more events associated with facility 114, or any other applicable information associated with permitting user 108 access to facility 114.

Figure 6:
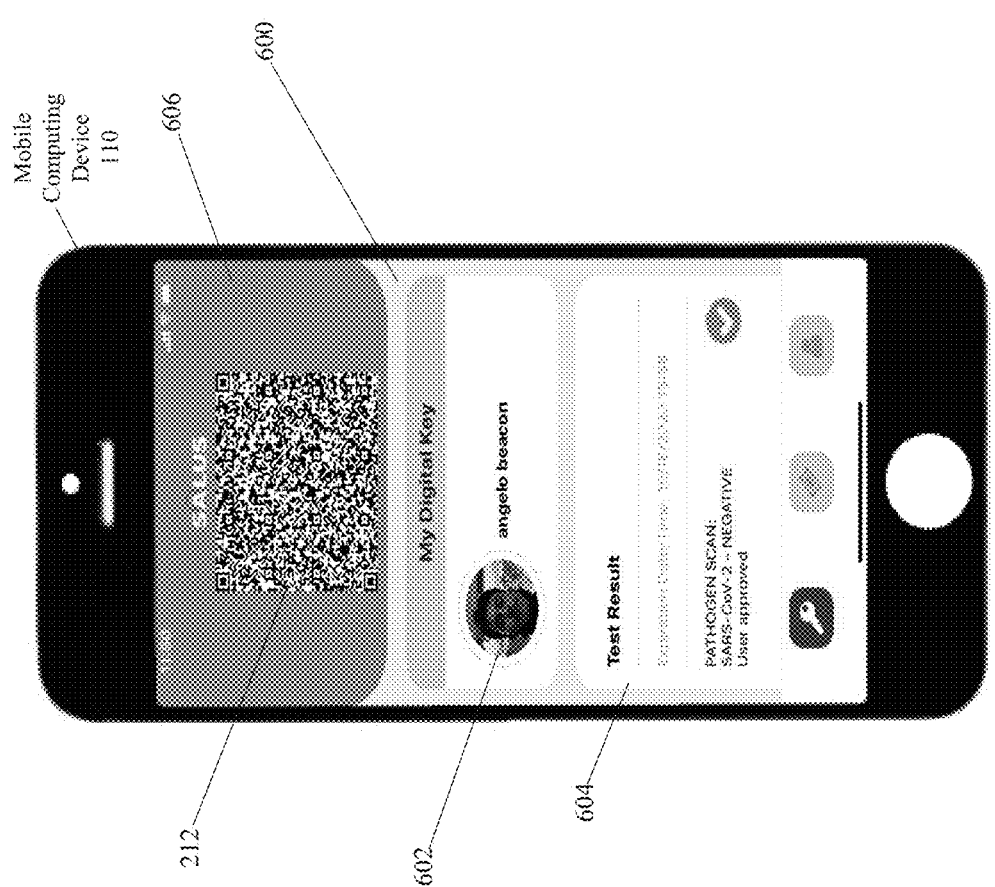
FIG. 6 illustrates an exemplary user interface for a facility admissions credential including a negative test result, according to an example embodiment.

At step 514, server 102 receives the results of the loaded infectious disease testing kit from IDT module 302 via transmission of the UITC. It is to be understood the UITC is configured to include the results of the test performed on the one or more biological samples included in the loaded infectious disease testing kit. Thus, at step 516, server 102 generates two-dimensional code 212 based on the UITC received from IDT module 302, wherein two-dimensional code 212 is configured to be activated by server 102 for the predetermined period of time based on determining, by server 102 analyzing UITC, that two-dimensional code 212 is valid for permitting user 108 access to facility 114. The determination that two-dimensional code 212 is valid for permitting user 108 access to facility 114 is based on the UITC indicating that the one or more biological samples tested negative for an infectious disease. At step 518, server 102 transmits two-dimensional code 212 to mobile computing device 110. It is to be understood that two-dimensional code 212 may be transmitted to mobile computing device 110 at any time after both user 108 is verified and the UITC indicates that user 108 tested negative for an infectious disease. At step 520, mobile computing device 110 receives two-dimensional code 212. An example user interface including an embodiment of two-dimensional code 212 presented via mobile computing device 110 is illustrated in FIG. 6, and will be discussed in greater detail in reference to FIG. 6. At step 522, user 108 presents mobile computing device 110 including two-dimensional code 212 to gatekeeper device 116 allowing gatekeeper device 116 to scan two-dimensional code 212 and permit user 108 entry to facility 114 based on facility credential 210 indicating user 108 tested negative for an infectious disease. At step 524, gatekeeper device 116 makes a determination relating to whether or not user 108 is infected based on facility credential 210 including the test result based on UITC. If UITC indicates that user 108 tested positive for an infectious disease, then step 526 occurs in which gatekeeper device 116 denies user 108 entry into facility 114 and server 102 advises user 108 to quarantine and/or take applicable medical next steps. If UITC indicates that user 108 tested negative for an infectious disease, then step 528 occurs in which gatekeeper device 116 permits user 108 entry into facility 114.

Referring now to FIG. 6, an exemplary negative facility admissions credential (facility credential 210) user interface 600 including a negative test result and resulting two-dimensional code 212 displayed on mobile computing device 110 is illustrated, according to an exemplary embodiment. In one embodiment, facility admission credential user interface 600 includes a profile image 602 of user 108 including the topical form identification captured during the process of submitting the biological samples to testing site 204, a test result 604, a color indicator 606 configured to reflect test result 604, and two-dimensional code 212. It is to be understood that server 102 may generate facility credential 210 including two-dimensional code 212 based on UITC allowing test result 604, received via UITC specific to user 108 from IDT module 302, to be integrated into facility credential 210. As depicted in FIG. 6, UITC indicates to server 102 that user 108 has tested negative for an infectious disease resulting in server 102 generating two-dimensional code 212 and associating two-dimensional code 212 with color indicator 606 emitting the color green indicating that user 108 is cleared for entry based on test result 604. Thus, when two-dimensional code 212 is scanned by gatekeeper device 116, user 108 is permitted access into facility 114.

Figure 7:
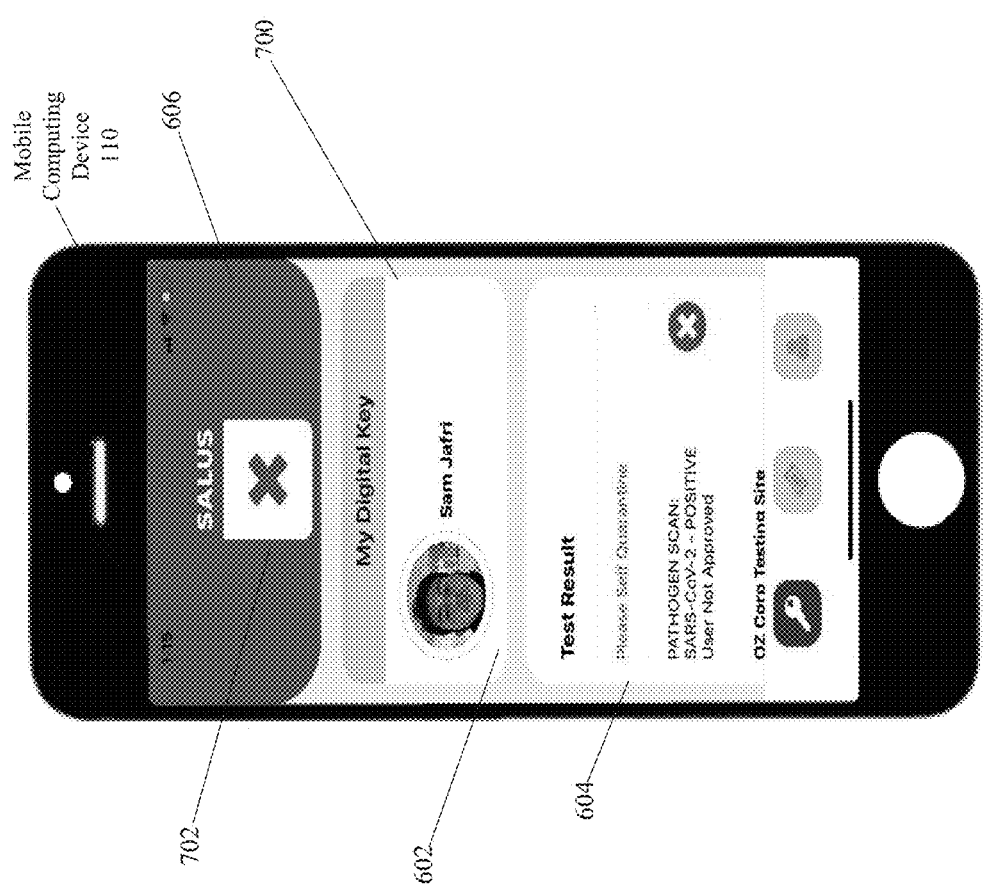
FIG. 7 illustrates an exemplary user interface for a facility admissions credential including a positive test result, according to an example embodiment.

Referring now to FIG. 7, an exemplary positive facility admission credential user interface 700 including a positive test result displayed on mobile computing device 110 is illustrated, according to an exemplary embodiment. In one embodiment, positive facility admission credential user interface 700 includes the topical form identification captured during the process of submitting the biological samples to testing site 204, the test result 604, and the color indicator 606 configured to reflect test result 604. As illustrated, facility admission credential user interface 700 purposely does not include two-dimensional code 212 due to the fact that in this example user 108 has tested positive for an infectious disease; hence, the color indicator 606 emits the color red indicating UITC is associated with a positive test result 604 resulting in user 108 not being allocated two-dimensional code 212 for entry into facility 114. It is to be understood that upon receiving the positive test result 604, server 102 may transmit one or more messages to mobile computing device 110 providing user 108 with applicable advice associated with the positive test result 604, such as "Please self quarantine". It is to be understood that facility admission credential user interfaces 600 & 700 and their components are configured to be event specific allowing system 100 to store a plurality of facility credentials 210 associated with the user personal profiles in database 104 and/or data storage module 318, wherein facility credentials 210 are configured to expire when the applicable event at facility 114 has ended.

Figure 8:
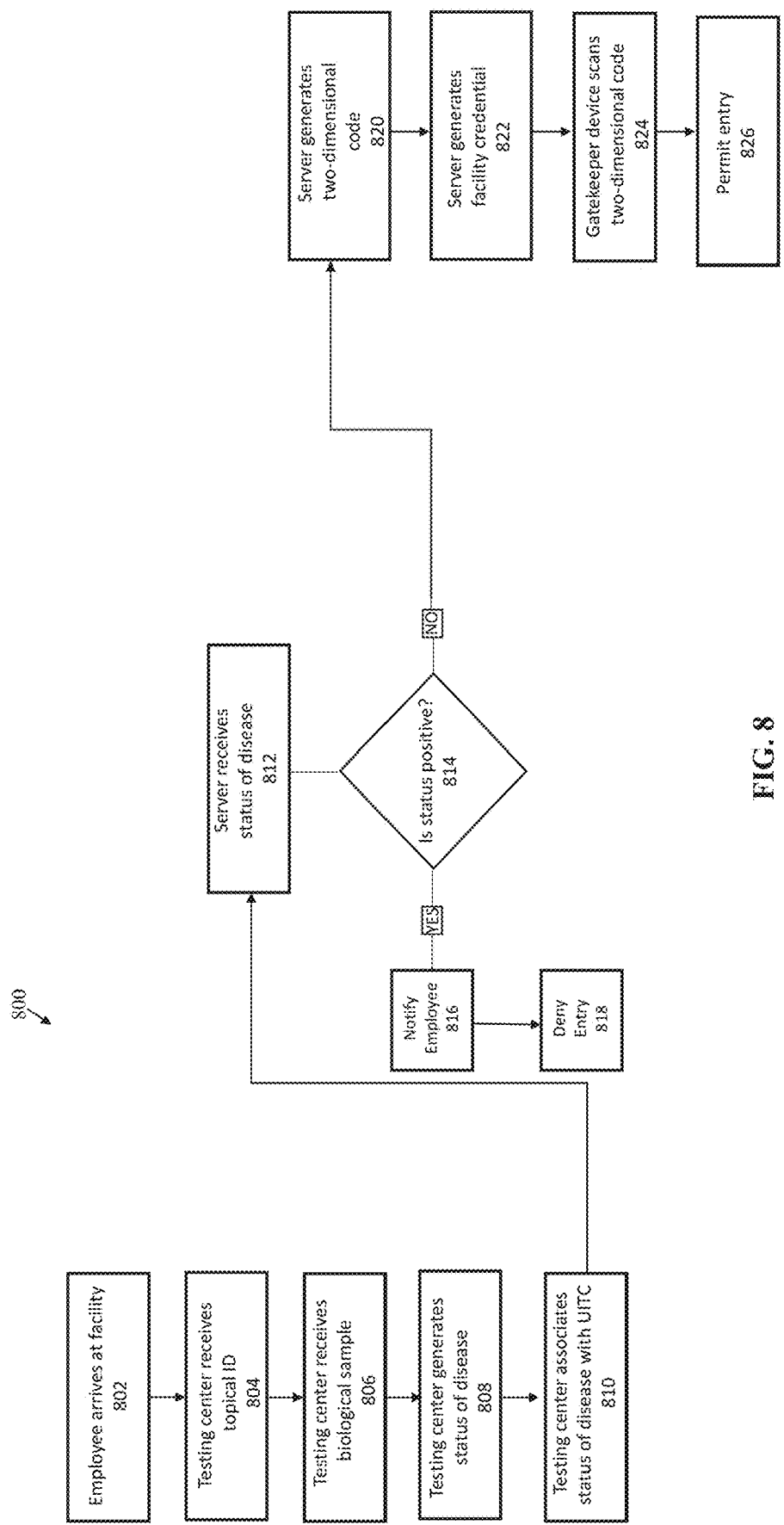
FIG. 8 is a block diagram illustrating an exemplary method for managing employee infectious disease dissemination, according to an example embodiment.

Referring now to FIG. 8, an exemplary method for managing employee infectious disease dissemination 800 is depicted, according to an example embodiment. It is to be understood that for the purpose of illustrating method 800 that user 108 may be referred to as an employee and facility 114 may be referred to as an employer facility, and testing site 204 is configured to be within the vicinity of the employer facility in order to allow on-site testing of employees in real-time. Furthermore, an employee may include, but is not limited to, an independent contractor, part-time worker, manager, board member, or any other individual configured to be associated with an entity offering consideration in exchange for services and an employer facility may be, but is not limited to a structure, cruise ship, or environment configured to facilitate common access control for said employees. At step 802, employee arrives at employer facility, wherein employee initializes the centralized platform in order to access employer facility. In one embodiment, employee is prompted by server 102 to upload the topical form of identification to server 102 which is transmitted to IDT module 302 in order to verify employee. At step 804, testing center 204 receives the topical form of identification is received from IDT module 302. In one embodiment, the topical form of identification is compared to a pre-existing form of identification associated with the employee to verify the identity of the employee. At step 806, testing center 204 receives one or more biological samples associated with the employee in which the one or more biological samples are applied to the unloaded infectious disease testing kit generating a loaded infectious disease testing kit, and wherein the unloaded infectious disease testing kit includes the UITC generated by UITC generator module 310. At step 808, testing center generates a status of an infectious disease of the employee based on the loaded infectious disease testing kit. At step 810, testing center 204 associates the status of the infectious disease with UITC for the employee based on the loaded infectious disease kit allowing the UITC to be configured to be transmitted in a manner that does not violate confidentiality of the employee due to the status of the infectious disease being directly linked to the UITC. At step 812, testing center 204 utilizes IDT module 302 to transmit the status of the infectious disease, via the UITC, to server 102. At step 814, server 102 determines whether the status of the infectious disease is positive or negative based on the UITC. If the status is positive, then step 816 occurs and server 102 notifies employee of their positive status and step 818 occurs in which gatekeeper device 116 denies entry to employee. Otherwise, if the status is negative then step 820 occurs in which server 102 generates two-dimensional code 212. At step 822, server 102 generates an employer facility credential including two-dimensional code 212. At step 824, gatekeeper device 114 scans two-dimensional code 212. At step 826, gatekeeper device 114 permits entry of employee to the employer facility.

Figure 9:
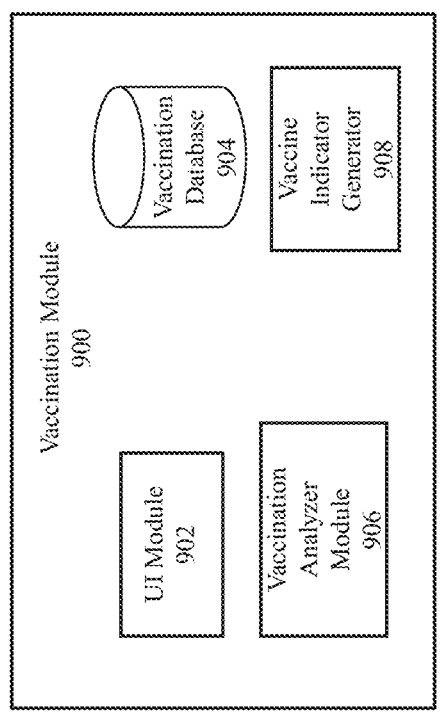
FIG. 9 illustrates a computer system according to exemplary embodiments of the present technology.

Referring now to FIG. 9, a vaccination module 900 along with associated user interfaces depicted on mobile computing device 110 are illustrated according to an exemplary embodiment. It is to be understood that vaccination module 900 is configured to receive a plurality of vaccination data associated with user 108 from mobile computing device 110 and/or a third party entity configured to handle vaccination data in a manner that does not violate data privacy regulations. The plurality of vaccination data may apply to one or more of whole virus vaccines, protein subunit vaccines, nucleic acid vaccines, viral vector vaccines, and/or any other applicable vaccine known those of ordinary skill in the art. The purpose of the plurality of vaccination data is to account for and ensure that user 108 has received all applicable vaccinations (in particular, COVID 19 vaccinations) and waited the predetermined periods of time after the most recent administration of the applicable vaccine required in order for server 102 to generate two-dimensional code 212 reflecting that user 108 is not only COVID 19 negative, but also effectively vaccinated. The plurality of vaccination data may be transmitted to vaccination module 900 from the aforementioned third party over network 106 and/or user 108 may manually provide the plurality of vaccination data; however, in the instance where user 108 manually provides the plurality of vaccination data it must still be authenticated by vaccination module 900 in order for server 102 to generate two-dimensional code 212. For example, in connection with the manual input, the user may be required to take a photo image of the vaccination card on his or her cell phone and upload the same to vaccination module 900. In this case, vaccination module 900 may have some confirmation sub-modules to confirm the authenticity of the vaccination card carried by the user and confirm/verify that the card is associated with user 108. In some embodiments, vaccination module 900 includes a vaccination user interface module 902, a vaccination data database 904, a vaccination analyzer module 906, and a vaccine indicator generator 908. In some embodiments, vaccination user interface module 902 generates one or more user interfaces (as depicted in FIGS. 10-14) configured to prompt for and display the plurality of vaccination data based on responses to said prompts for the plurality of vaccination data. The plurality of vaccination data may be stored in vaccination database 904, wherein vaccination database 904 may be coupled to, derived from, and/or associated with database 104. Vaccination database 904 may include one or more vaccination records of user 108 in which the vaccination records are configured to be continuously updated in order to particularly account for instances in which one or more doses of vaccinations (and vaccination intervals) are necessary.

Figure 10:
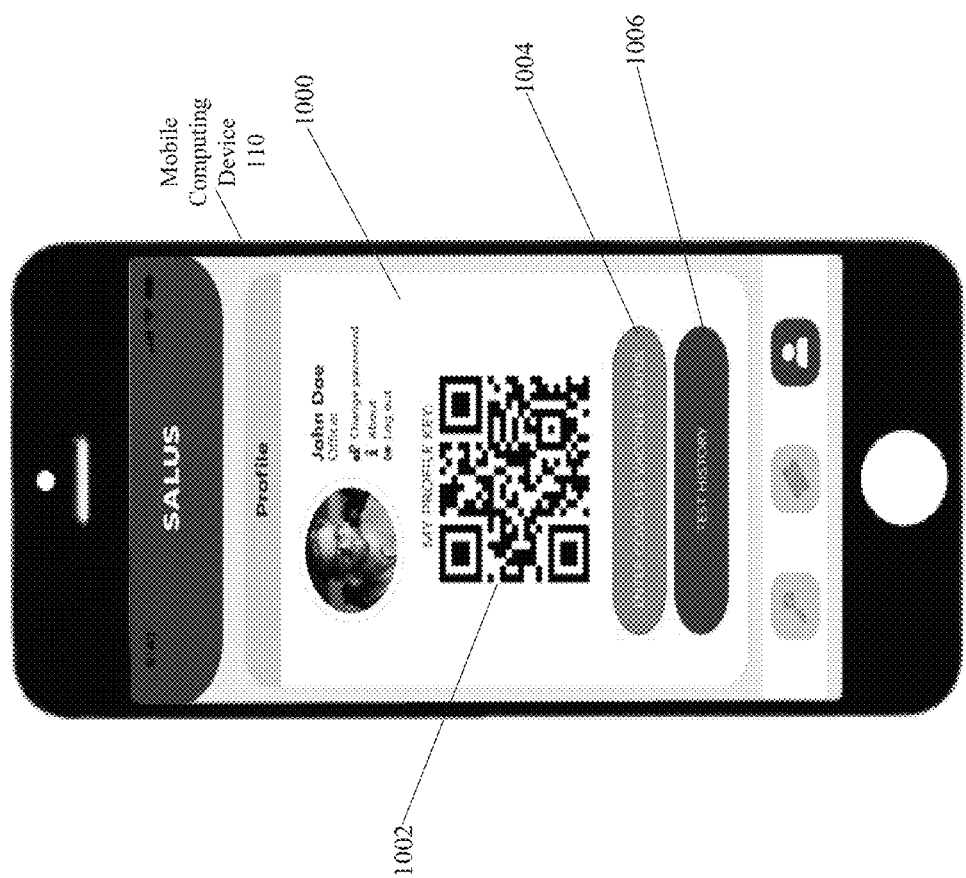
FIG. 10 depicts a user vaccination profile interface associated with user generated by vaccination user interface module depicted on mobile computing device.

For example, FIG. 10 depicts a user vaccination profile interface 1000 associated with user 108 generated by vaccination user interface module 902 depicted on mobile computing device 110, according to an exemplary embodiment. In some embodiments, user vaccination profile interface 1000 includes a user profile key 1002, a vaccination status input button 1004, and a test history button 1006. The user profile key 1002 may be a scannable QR code or any other identifiable code configured to be scanned by a scanning device associated with at least one of facility 114, testing site 204, infectious disease testing module 302, equipment module 322, or any other applicable entity of system 100 that wishes to verify user 108, and in some instances user profile key 1002 provides the applicable party access to real-time updates concerning applicable information associated with user 108. In some embodiments, user profile key 1002 is configured to direct the applicable user of the scanning device (testing proctor) to applicable information associated with user 108 derived from user personal profile module 312; however, user profile key 1002 is intended to depict an image of user 108 for verification purposes at testing site 204 in addition to provide a contactless mechanism for the testing proctor to add user 108 into a testing queue at testing site 204 upon scanning. In some embodiments, profile key 1002 may be the scannable authentication token configured to be created by at least one of server 102, UITC generator module 310, and/or an applicable server associated with testing site 204 allowing profile key 1002 to not only function as the user supplied means to assist user 108 being associated with UITC, but also account for updates associated with the results of the test for the infectious disease. For example, the applicable individual rendering the test at testing site 204 may use the scanning device to scan profile key 1002 and scan the UITC in order to associate user 108 with the UITC. Upon scanning of profile key 1002 and UITC, server 102 associates user 108 with the results of the infectious disease test derived from scanning the testing kit two-dimensional code. Thus, not only does profile key 1002 prevent user 108 from handing mobile computing device 110 over to the testing proctor, but also profile key 1002 may serve as the mechanism for the testing result derived from the testing kit two-dimensional code being associated with UITC and/or user 108 altogether.

In some embodiments, user 108 uses user vaccination profile interface 1000 to direct him/her to an applicable user interface depicting the plurality of vaccination data if it has already been provided to and verified by vaccination module 900. Test history button 1006 directs user 108 to an applicable user interface depicting a listing of the times and dates associated with infectious disease statuses of user 108 along with supporting test results provided by IDT module 302. The aforementioned data is also configured to be stored on vaccination database 904 in order to assist vaccination analyzer module 906 to provide a vaccination analysis when vaccination module 900 receives the plurality of vaccination data. It is to be understood that vaccination analyzer module 906 is configured to verify the plurality of vaccination data regardless of whether it is provided by user 108 or an applicable third party.

Figure 11:
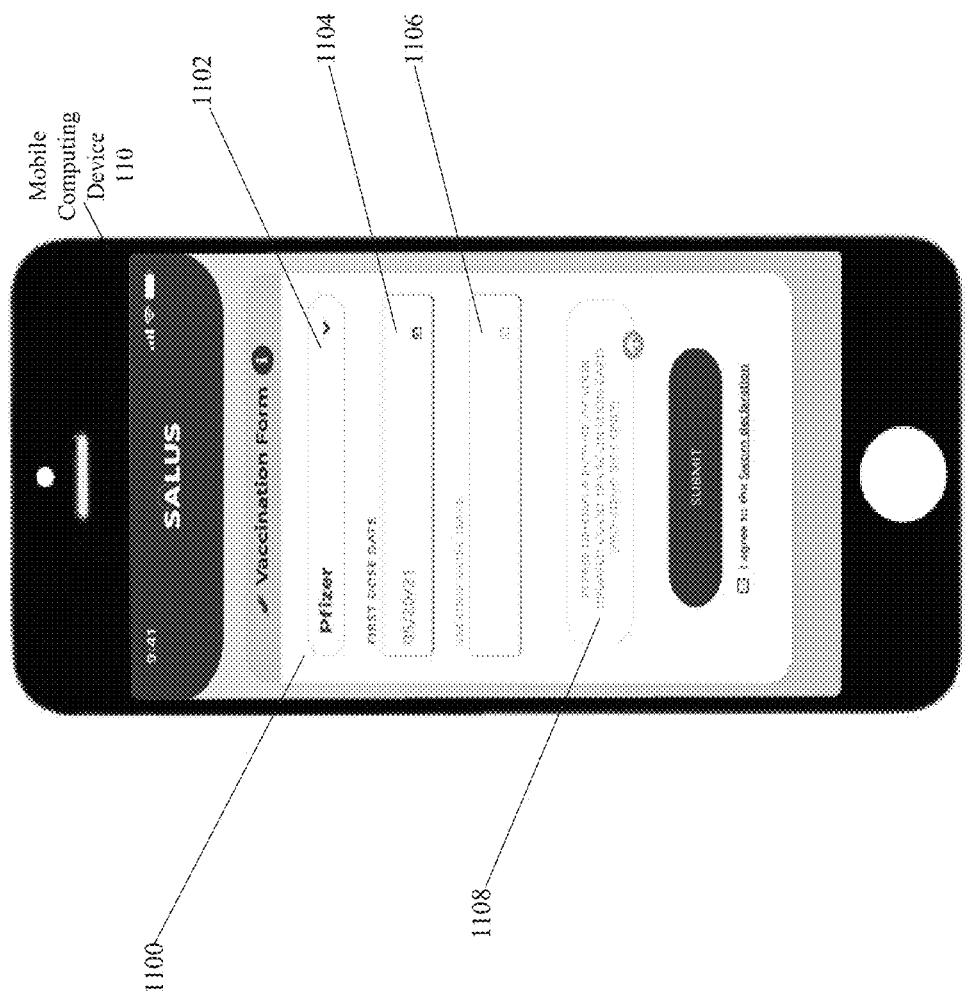
FIG. 11, shows a vaccination form user interface on a mobile computing device.

Referring now to FIG. 11, a vaccination form user interface 1100 is depicted on mobile computing device 110 which user 108 is directed to upon selection of vaccination status input button 1004. Vaccination form user interface 1100 is generated by vaccination user interface module 902 allowing user 108 to manually input the plurality of vaccination data on mobile computing device 110. In some embodiments, vaccination form user interface 1100 includes a vaccination type data field 1102, a first vaccination dose data field 1104, a second vaccination dose data field 1106, and a vaccination attestation upload data field 1108. It is to be understood that vaccination module 900 is designed and configured to account for single-dose and multiple-dose vaccination distribution; however, in some embodiments, availability of first vaccination dose data field 1104 and second vaccination dose data field 1106 to user 108 is based upon the type of vaccination entered into vaccination type data field 1102. For example, if the vaccination type is the J&J/Janssen COVID-19 vaccine which requires only a single dose then second vaccination dose data field 1106 is inapplicable and user 108 must wait the predetermined period of time prior to server 102 generating two-dimensional code 212. In another example, if the vaccination type is the Moderna or Pfizer vaccine, then user 108 must enter the date of the first dose administration in first vaccination dose data field 1104, and the second vaccination dose data field 1106 is not available for entry of data by user 108 until at least 14 days after the date reflected in first vaccination dose data field 1104 verified by vaccination analyzer module 906. This is to ensure that user 108 is waiting the Centers for Disease Control and Prevention (CDC) recommended timeframe between doses (if applicable) along with after the last dose. In some embodiments, input into vaccination attestation upload data field 1108 requires user 108 to utilize the camera on mobile computing device 110 in order to scan and upload an image of a vaccination card certifying that user 108 did in fact receive one or more of the aforementioned doses.

Figure 12:
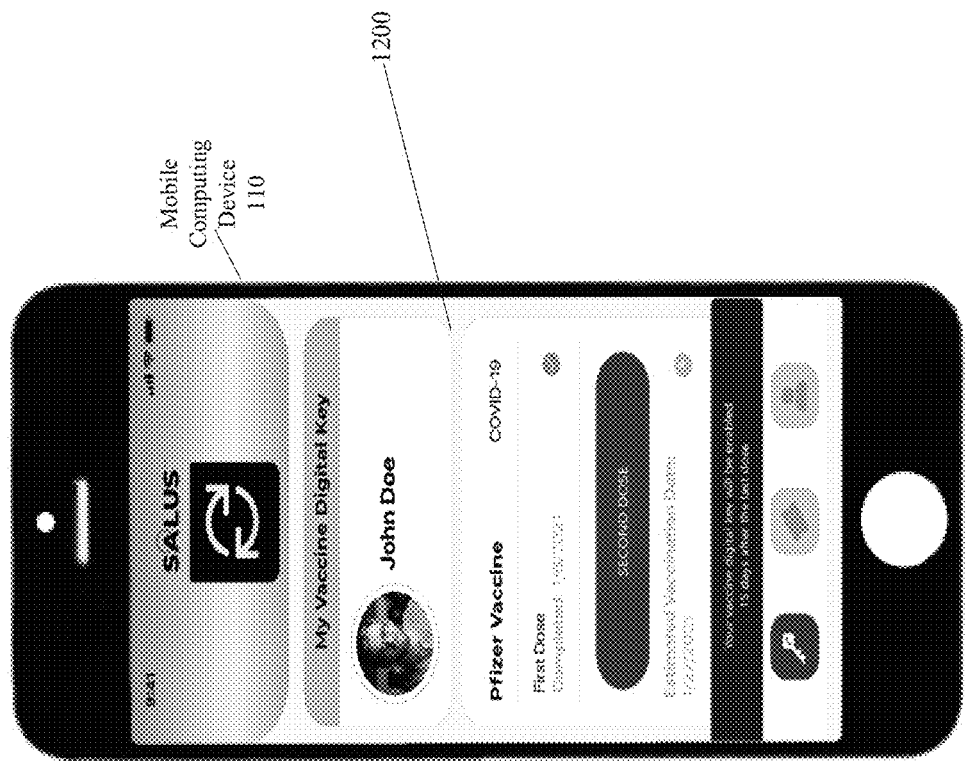
FIG. 12 shows a first vaccination dosage confirmation user interface.

Referring now to FIG. 12, a first vaccination dosage confirmation user interface 1200 is depicted on mobile computing device 110, according to an exemplary embodiment, in which first vaccination dosage confirmation user interface 1200 illustrates that the first dosage of the vaccination has been completed, and vaccination module 900 calculates a projected dose date for user 108 to receive the second dosage of the vaccination. For example, first vaccination dosage confirmation user interface 1200 depicts that user 108 completed the first dose of the Pfizer vaccine on Jan. 6, 2021 and the second vaccination dosage is estimated to be received on Jan. 27, 2021 in which second vaccination dose data field 1106 will not be able be filled by user 108 until said date, allowing user 108 to be in compliance with CDC and/or vaccination guidelines.

Figure 13:
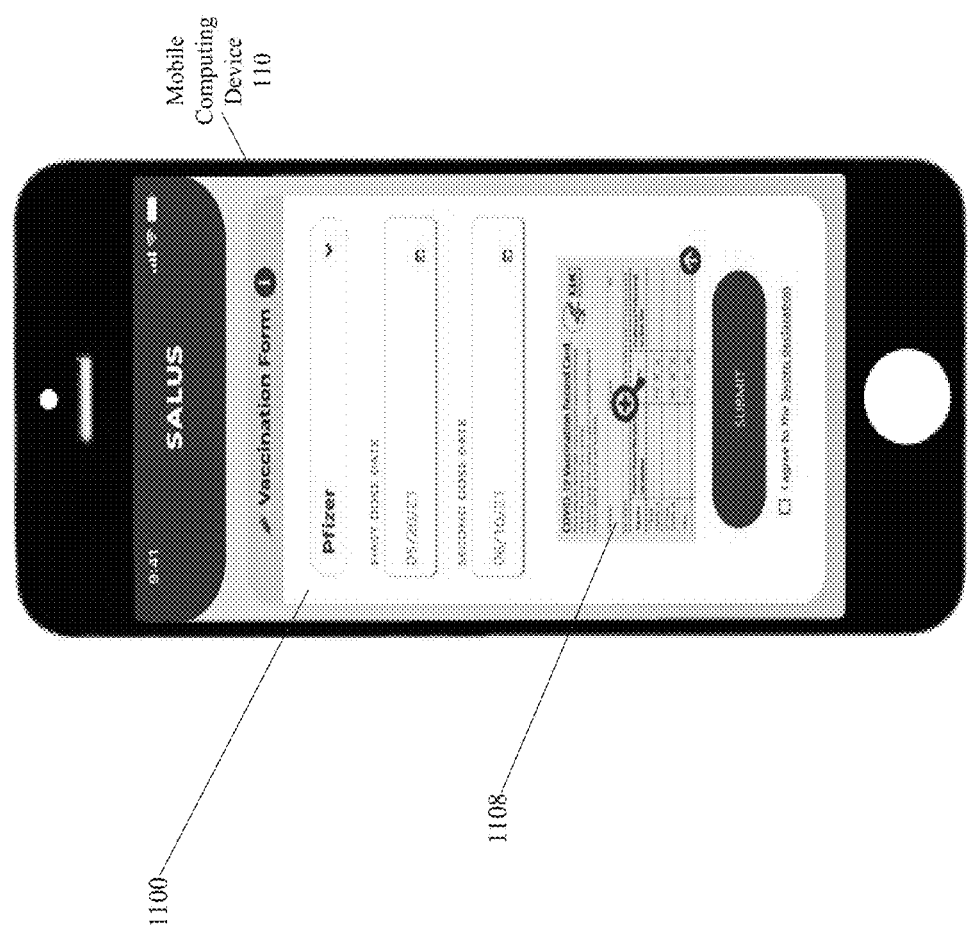
FIG. 13 shows a vaccination form user interface illustrating the acquired image of the vaccination card.

Referring now to FIG. 13, vaccination form user interface 1100 is depicted on mobile computing device 110 illustrating the acquired image of the vaccination card acquired from the camera of mobile computing device 110 within vaccination attestation upload data field 1108. In some embodiments, vaccination analyzer module 906 may be configured to utilize optical character recognition (OCR) in order to extract the plurality of vaccination data from the vaccination card via an image acquired of the vaccination card via the at least a sensor (i.e., camera) of mobile computing device 110. Vaccination analyzer module 906 is configured to verify the plurality of vaccination data extracted from the vaccination card, and automatically load the plurality of vaccination data into vaccination type data field 1102 (vaccination manufacturer), first vaccination dose data field 1104 (first vaccination dose data), and second vaccination dose data field 1106 (second vaccination dose data) respectively upon verification. It is to be understood that regardless of the plurality of vaccination data being entered manually via user 108, provided by the applicable third party entity, or extracted from the vaccination card, vaccination module 900 is required to authenticate the data within first vaccination dose data field 1104 and second vaccination dose data field 1106 in order for vaccine indicator generator 908 to generate a vaccine indicator representing that user 108 has been properly and effectively vaccinated within the predetermined period of time, wherein the vaccine indicator is configured to be received by server 102 for the purpose of being used as a requirement that must be satisfied in order for server 102 to generate two-dimensional code 212.

Figure 14:
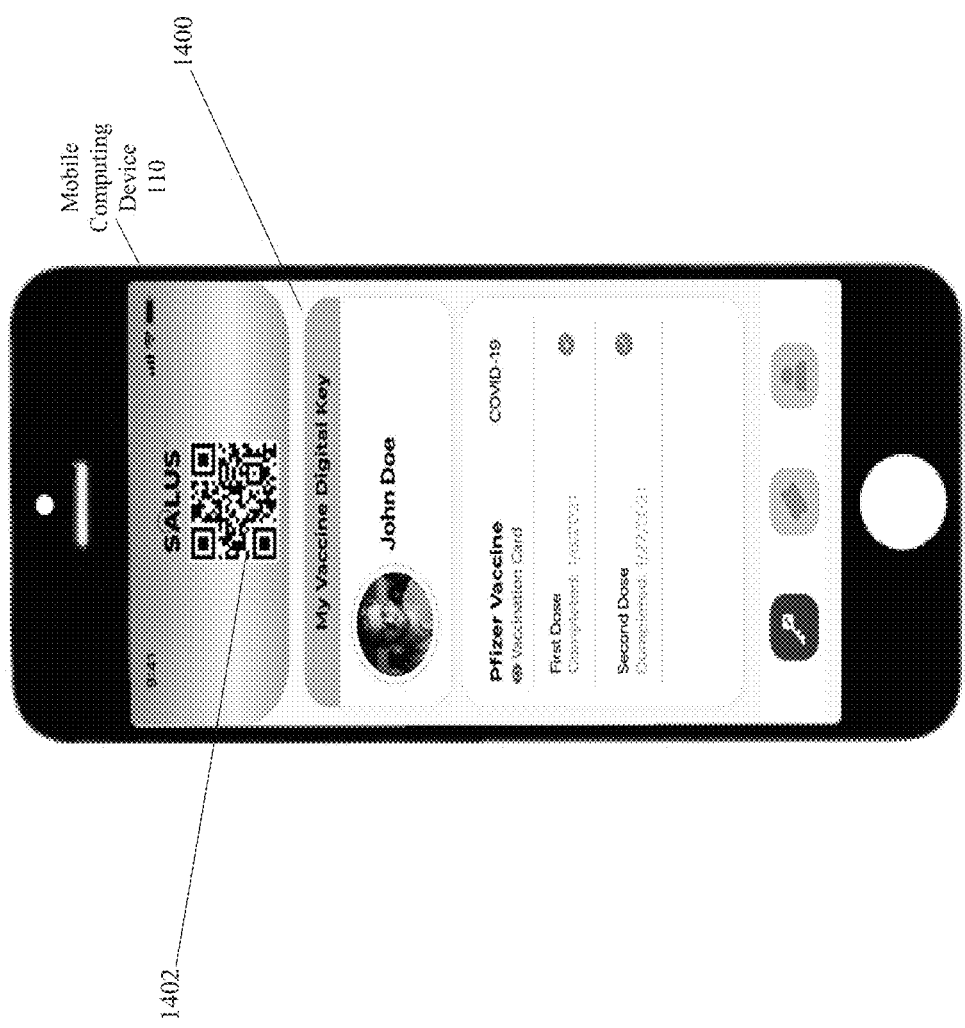
FIG. 14 depicts a vaccine digital key user interface.

Referring now to FIG. 14, a vaccine digital key user interface 1400 is depicted on mobile computing device 110, according to an exemplary embodiment. In some embodiments, vaccine digital key user interface 1400 includes a vaccine-based two-dimensional code 1402 generated by server 102, alone or in combination with vaccination module 900, based on the vaccine indicator received by server 102 over network 106. It is to be understood that vaccine-based two-dimensional code 1402 may be two-dimensional code 212 and/or a derivative of two-dimensional code 212 generated by server 102 based on the vaccine indicator indicating that user 108 received the applicable vaccination dose (first and/or second dose) or final vaccination dose within the predetermine time period prior to generation. In some embodiments, activation of two-dimensional code 212 by server 102 is based on the vaccine indicator indicating that user 108 has been effectively vaccinated for the infectious disease. In some embodiments, vaccine-based two-dimensional code 1402 includes an encrypted digital key configured to function as a security mechanism preventing another user of system 100 from gaining access to facility 114 with vaccine-based two-dimensional code 1402 that was not intended for them. It is to be understood that in certain embodiments, the QR code depicted on vaccine digital key user interface 1400 is user profile key 1002 configured to be scanned by the scanning device of testing site 204 in order for server 102 to associate the UITC with user 108.

Figure 15:
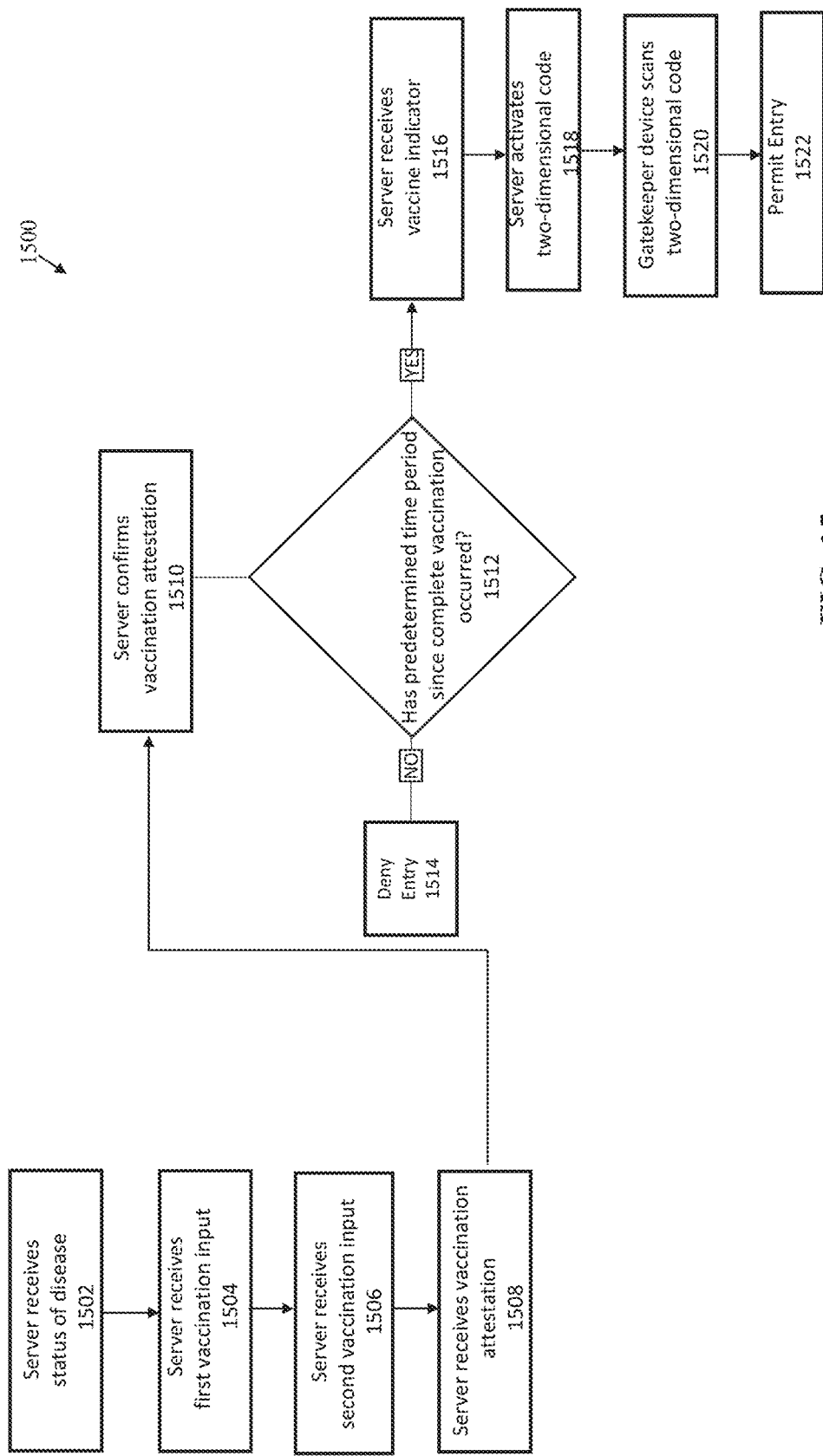
FIG. 15 depicts a method for managing dissemination of infectious diseases based on vaccination credentials.

Referring now to FIG. 15, an exemplary method for managing dissemination of infectious diseases based on vaccination credentials 1500 is depicted, according to an example embodiment. At step 1502, server 102 receives the results of the loaded infectious disease testing kit from IDT module 302 via transmission of the UITC. Under the assumption that user 108 receives a negative status for the infectious disease at step 1502, at step 1504, server 102 receives a first validated vaccination input of the plurality of vaccination data from vaccination module 900 provided on vaccination form user interface 1100 in which is validated by vaccination module 900 and/or the applicable verification entity. At step 1506, server 102 receives a second validated vaccination input of the plurality of vaccination data from vaccination module 900 in which server 102 assumes to be validated by vaccination module 900 and/or the applicable verification entity. At step 1508, server 102 receives a vaccination attestation, such as a vaccination card, or any other application vaccination confirmation data from vaccination module 900. At step 1510, server 102 confirms the plurality of vaccination data matches data contained on the vaccination attestation via vaccination analyzer module 906. At step 1512, server 102 makes a determination as to whether the predetermined time period has occurred since the most recent vaccination received by user 108 was administered. For example, server 102 may determine that it has been 15 days since the second dose of the Moderna vaccination has been administered to user 108 indicating that user 108 has been properly and effectively vaccinated. If not, then step 1514 occurs in which server 102 does not activate two-dimensional code 212 and/or vaccine-based two-dimensional code 1402 resulting in gatekeeper device 116 denying user 108 access into facility 114 by server 102 not activating two-dimensional code 212 and/or vaccine-based two-dimensional code 1402 due to server 102 not receiving the vaccine indicator. Otherwise, step 1516 occurs in which server 102 receives the vaccine indicator generated by vaccine indicator generator 908 from vaccination module 900. At step 1518, two-dimensional code 212 and/or vaccine-based two-dimensional code 1402 is generated and/or activated based on the vaccine indicator received from vaccination module 900. At step 1520, user 108 presents mobile computing device 110 including two-dimensional code 212 and/or vaccine-based two-dimensional code 1402, as illustrated in FIG. 14, to gatekeeper device 116 allowing gatekeeper device 116 to scan two-dimensional code 212 and/or vaccine-based two-dimensional code 1402. At step 1522, gatekeeper device 116 scans two-dimensional code 212 and/or vaccine-based two-dimensional code 1402 and permits user 108 entry into facility 114.

Figure 16:
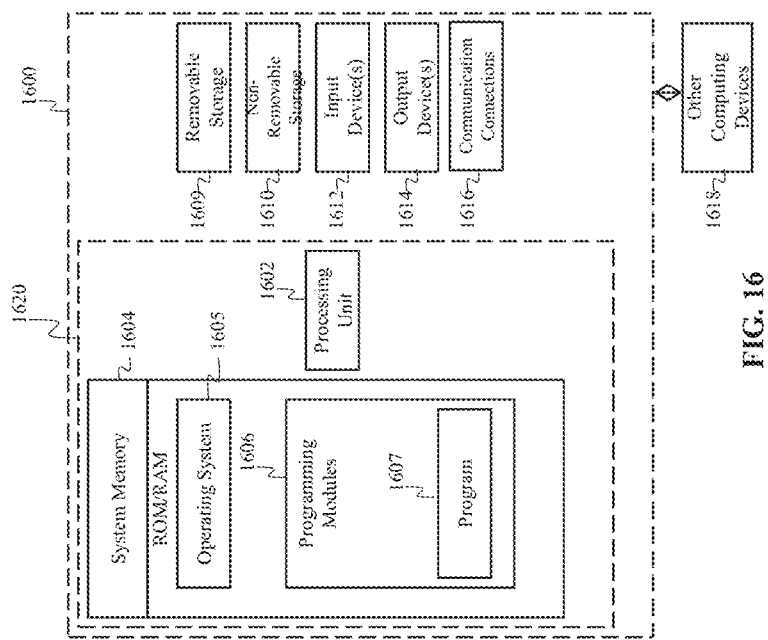
FIG. 16 is a block diagram of a system including an exemplary computing device and other computing devices.

FIG. 16 is a block diagram of a system including an example computing device 1600 and other computing devices. Consistent with the embodiments described herein, the aforementioned actions performed by devices 110, 112, 116, and server 102 may be implemented in a computing device, such as the computing device 1600 of FIG. 16. Any suitable combination of hardware, software, or firmware may be used to implement the computing device 1600. The aforementioned system, device, and processors are examples and other systems, devices, and processors may include the aforementioned computing device. Furthermore, computing device 1600 may include an operating environment for system 100 and processes/methods 500, 800, & 1500. Processes 500, 800, & 1500, and data related to said processes may operate in other environments and are not limited to computing device 1600.

With reference to FIG. 16, a system consistent with an embodiment of the invention may include a plurality of computing devices, such as computing device 1600. In a basic configuration, computing device 1600 may include at least one processing unit 1602 and a system memory 1604. Depending on the configuration and type of computing device, system memory 1604 may include, but is not limited to, volatile (e.g. random access memory (RAM)), non-volatile (e.g. read-only memory (ROM)), flash memory, or any combination or memory. System memory 1604 may include operating system 1605, and one or more programming modules 1606. Operating system 1605, for example, may be suitable for controlling computing device 1600's operation. In one embodiment, programming modules 1606 may include, for example, a program module 1607 for executing the actions of server 102 and devices 110, 112, and 116, for example. Furthermore, embodiments of the invention may be practiced in conjunction with a graphics library, other operating systems, or any other application program and is not limited to any particular application or system. This basic configuration is illustrated in FIG. 16 by those components within a dashed line 1620.

Computing device 1600 may have additional features or functionality. For example, computing device 1600 may also include additional data storage devices (removable and/or non-removable) such as, for example, magnetic disks, optical disks, or tape. Such additional storage is illustrated in FIG. 16 by a removable storage 1609 and a non-removable storage 1610. Computer storage media may include volatile and nonvolatile, removable and non-removable media implemented in any method or technology for storage of information, such as computer readable instructions, data structures, program modules, or other data. System memory 1604, removable storage 1609, and non-removable storage 1610 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1600. Any such computer storage media may be part of device 1600. Computing device 1600 may also have input device(s) 1612 such as a keyboard, a mouse, a pen, a sound input device, a camera, a touch input device, etc. Output device(s) 1614 such as a display, speakers, a printer, etc. may also be included. The aforementioned devices are only examples, and other devices may be added or substituted.

Computing device 1600 may also contain a communication connection 1616 that may allow device 1600 to communicate with other computing devices 1618, such as over a network in a distributed computing environment, for example, an intranet or the Internet. Communication connection 1616 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 1604, including operating system 1605. While executing on processing unit 1602, programming modules 1606 (e.g. program module 1607) may perform processes including, for example, one or more of the stages of the processes 500, 800, & 1500 as described above. The aforementioned processes are examples, and processing unit 1602 may perform other processes. Other programming modules that may be used in accordance with embodiments of the present invention may include electronic mail and contacts applications, word processing applications, spreadsheet applications, database applications, slide presentation applications, drawing or computer-aided application programs, etc.

The claims appended hereto are meant to cover all modifications and changes within the scope and spirit of the present invention.

What is claimed is:

1. A method for infectious disease prevention comprising:
   transmitting, via a server, a facility credential associated with a facility configured to identify a user operating on an application deployed by the server;
   receiving, via the server, a user identification test code (UITC) associated with a status of an infectious disease of the user;
   generating a two-dimensional code configured to be associated with the facility credential based on the UITC;
   activating, via the server, the two-dimensional code for a predetermined period of time based on a vaccine indicator received by the server indicating the user has received a vaccination for the infectious disease;
   reading, via a gatekeeper device, the two-dimensional code; and
   permitting, via the gatekeeper device, the user access to the facility based on the facility credential and the two-dimensional code.

2. The method of claim 1, wherein receiving the UITC further comprises:
   receiving, via the server, a plurality of vaccination data associated with the user;
   storing, via the server, the plurality of vaccination data in a vaccination database operated by a vaccination module; and
   generating, via the vaccination module, the vaccine indicator.

3. The method of claim 2, wherein receiving the plurality of vaccination data comprises:
   scanning, via the vaccination module, a vaccination card associated with the user; and
   determining, via the vaccination module, if the user received at least one vaccination for the infectious disease within an established period of time based on the plurality of vaccination data.

4. The method of claim 2, wherein receiving the plurality of vaccination data comprises:
   receiving, via the vaccination module, a plurality of vaccination inputs indicating the user received at least one vaccination for the infectious disease within an established period of time.

5. The method of claim 1, wherein the vaccine indicator is an encrypted digital vaccination key generated by a vaccination module communicatively coupled to the server.

6. The method of claim 5, wherein the vaccination module is configured to transmit the vaccine indicator to the server to activate the encrypted digital vaccination key based on the vaccination module detecting a most recent vaccination of a plurality of vaccinations associated with the user administered at least 15 days before.

7. A method for employee infectious disease prevention comprising:
   transmitting, via a server, to a mobile computing device, an employer facility credential associated with an employer facility configured to identify an employee;
   receiving, via the server, a user identification test code (UITC) associated with a status of an infectious disease of the employee;
   generating, via the server, a two-dimensional code associated with the employer facility credential based on the UITC;
   activating, via the server, the two-dimensional code based on a vaccine indicator received by the server indicating the employee has received at least a vaccination for the infectious disease;
   reading, via a gatekeeper device, the employer facility credential on the mobile computing device; and
   permitting, via the gatekeeper device, the employee access to the facility based on the employer facility credential and the two-dimensional code.

8. The method for employee infectious disease prevention of claim 7, further comprising:
   scanning, via an infectious disease testing module, an unloaded infectious disease test kit at a testing site.

9. The method for employee infectious disease prevention of claim 7, further comprising:
   tracking, via the server, the geographic location of the mobile computing device.

10. The method for employee infectious disease prevention of claim 7, further comprising:
    defining, via the server or the gatekeeper device, at least one geofence based on a geographic proximity relative to the facility.

11. The method for employee infectious disease prevention of claim 10, further comprising:
    deactivating, via the server or the gatekeeper device, the two-dimensional code based upon the server or gatekeeper device detecting the mobile computing device outside of the at least one geofence.

12. The method for employee infectious disease prevention of claim 10, further comprising:
    deactivating, via the server or the gatekeeper device, the two-dimensional code based upon the server or the gatekeeper device detecting the mobile computing device outside of the at least one geofence for a predetermined period of roaming.

13. The method for employee infectious disease prevention of claim 7, wherein generating the two-dimensional code is based on a vaccine indicator, generated by a vaccination module, received by the server indicating the employee has received one or more vaccinations for the infectious disease.

14. The method for employee infectious disease prevention of claim 7, wherein receiving the UITC further comprises:
    receiving, via the server, a plurality of vaccination data associated with the employee;
    storing, via the server, the plurality of vaccination data in a vaccination database operated by a vaccination module; and generating, via the vaccination module, the vaccine indicator.

15. The method for employee infectious disease prevention of claim 14, wherein receiving the plurality of vaccination data comprises:
- scanning, via the vaccination module, a vaccination card associated with the employee; and
- determining, via the vaccination module, if the employee received at least one vaccination for the infectious disease within an established period of time based on the plurality of vaccination data.

16. The method for employee infectious disease prevention of claim 14, wherein receiving the plurality of vaccination data comprises:
- receiving, via the vaccination module, a plurality of vaccination inputs indicating the employee received at least one vaccination for the infectious disease within an established period of time.

17. A method for infectious disease prevention comprising:
- transmitting, via a server, a facility credential associated with a facility configured to identify a user operating on an application deployed by the server;
- receiving, via the server, a user identification test code (UITC) associated with a status of an infectious disease of the user;
- generating a two-dimensional code configured to be associated with the facility credential based on the UITC, wherein generating the two-dimensional code is based on a vaccine indicator received by the server indicating the user has received a vaccination;
- activating, via the server, the two-dimensional code on a substrate for a predetermined period of time;
- reading, via a gatekeeper device, the two-dimensional code from the substrate; and
- permitting, via the gatekeeper device, the user access to the facility based on the facility credential and the two-dimensional code.

18. The method for infectious disease prevention of claim 17, wherein generating the two-dimensional code is based on a vaccine indicator, generated by a vaccination module, received by the server indicating the user has received one or more vaccinations for the infectious disease.

19. The method for infectious disease prevention of claim 17, wherein receiving the UITC further comprises:
- receiving, via the server, a plurality of vaccination data associated with the user;
- storing, via the server, the plurality of vaccination data in a vaccination database operated by a vaccination module; and
- generating, via the vaccination module, the vaccine indicator.

20. The method for infectious disease prevention of claim 19, wherein receiving the plurality of vaccination data comprises:
- scanning, via the vaccination module, a vaccination card associated with the user; and
- determining, via the vaccination module, if the user received at least one vaccination for the infectious disease within an established period of time based on the plurality of vaccination data.

* * * * *